United States Patent [19]

Bisset et al.

[11] Patent Number: 5,561,133
[45] Date of Patent: Oct. 1, 1996

[54] THYMIDYLATE SYNTHASE INHIBITING QUINAZOLINONES

[75] Inventors: Graham M. F. Bisset; Vassilios Bavetsias, both of Sutton, England

[73] Assignee: British Technology Group Limited, London, England

[21] Appl. No.: 284,552

[22] PCT Filed: Mar. 16, 1993

[86] PCT No.: PCT/GB93/00540

§ 371 Date: Aug. 9, 1994

§ 102(e) Date: Aug. 9, 1994

[87] PCT Pub. No.: WO93/19051

PCT Pub. Date: Sep. 30, 1993

[30] Foreign Application Priority Data

Mar. 18, 1992 [GB] United Kingdom ............... 9205907

[51] Int. Cl.[6] ............... C07D 239/95; C07D 239/96; A61K 31/505; A61K 31/44

[52] U.S. Cl. ............... 514/259; 514/260; 514/19; 544/284; 544/285; 544/287

[58] Field of Search ............... 544/284, 287, 544/285; 514/259, 260

[56] References Cited

U.S. PATENT DOCUMENTS

| | | | |
|---|---|---|---|
| 4,447,608 | 5/1984 | Jones et al. | 514/259 |
| 4,564,616 | 1/1986 | Jones et al. | 514/259 |
| 4,746,659 | 5/1988 | DeGraw et al. | 514/259 |
| 4,767,761 | 8/1988 | Rosowsky | 514/259 |
| 4,981,856 | 1/1991 | Hughes | 514/259 |
| 4,985,441 | 1/1991 | Hughes et al. | 514/259 |
| 4,992,550 | 2/1991 | Hughes | 514/259 |
| 4,996,207 | 2/1991 | Nair et al. | 514/259 |
| 5,081,124 | 1/1992 | Hughes | 514/259 |
| 5,089,499 | 2/1992 | Barker et al. | 514/259 |
| 5,112,837 | 5/1992 | Burrows et al. | 514/259 |
| 5,187,167 | 2/1993 | Hughes | 514/259 |
| 5,236,927 | 8/1993 | Jones et al. | 514/259 |
| 5,252,573 | 10/1993 | Barker et al. | 514/259 |
| 5,280,027 | 1/1994 | Andrew et al. | 514/259 |

FOREIGN PATENT DOCUMENTS

| | | |
|---|---|---|
| 0031237 | 7/1981 | European Pat. Off. . |
| 0204529 | 10/1986 | European Pat. Off. . |
| 0239362 | 9/1987 | European Pat. Off. . |
| 0268377 | 5/1988 | European Pat. Off. . |
| 0451836A2 | 10/1991 | European Pat. Off. . |
| 0492316A1 | 7/1992 | European Pat. Off. . |
| 0509643A1 | 10/1992 | European Pat. Off. . |

OTHER PUBLICATIONS

E. Sikora et al. "Formation and Retention. . . " Biochem. Pharmacol. vol. 37 No. 21, (1988), pp. 4047–4054.
W. Thomas Mueller et al. "Inhibition of chicken liver. . ." Biochem. Pharmacol. vol. 37 No. 3, (1988), pp. 449–451.
Ka–yun Ng et al. "Liposome–dependent delivery. . ." Biochimica et Biophyisica Acta 981 (1989), pp. 261–268.
K, Pawalczak et al. "Quanazoline antifolates inhibiting. . . " J. Med. Chem. 1989, 32, pp. 160–165.

U. Kuefner et al. "Occurreance and significance of diastereomers. . ." Biochemistry 1990, 29, pp. 10540–10545.
G. M. F. Bisset et al. "Syntheses and thymidylate synthase. . ." Reprinted from Jour of Medicinal Chemistry, 1992, 35, pp. 859–866.
J, Galivan et al. "Y–fluoromethotrexate: Synthesis. . ." Proc. Natl. Acad. Sci. USA vol. 82 (May 1985), pp. 2598–2602.
J. J. McGuire et al. "Biochemical & Growth inhibitory. . ." Cancer Research 49 (Aug. 15, 1989), pp. 4517–4525.
J. K. Coward et al. "Fluoroglutamate–Containing folates. . ." Chemistry and Biology of Pteridines 1989, pp. 1200–1202.
T. C. Stephens et al. "Use of murine L5178Y" Chem. & Biol. of Pteridines & Folates, New York, 1993, pp. 589–592.
A. H. Calvert et al. "A phase I evaluation. . ." Jour. of Clinical Oncol. vol. 4 No. 8 (Aug. 1986), pp. 1245–1252.
B. M. J. Cantwell et al. "Phase II study of a novel antifolate. . ." Cancer Treatment Reports vol. 70 No. 11, Nov. 1986, pp. 1335–1336.
M. F. Bassendine et al. "Induction of remission. . ." Jour. of Hepatology, 1987, 4, pp. 349–356.
B. M. J. Cantwell et al. "Phase II study of the antifolate. . ." Euro. Jour. of Cancer Clin. Oncol., vol. 24 No. 4, 1988, pp. 733–736.
C. Sessa et al. "Phase I study of the antifolate. . ." Euro. Jour. of Cancer Clin. Oncol. vol. 24 No. 4, 1988, pp. 769–775.
Jackman et al., "Activity of the Thymidylate Synthase Inhibitor 2–Desamino–N[10]–propargyl–5,8–dideazafolic acid. . .", Cancer Reserach 50, 5212–5218(1990).
Jodrell et al., "The in vivo Metabolic Stability of Dipeptide Analogues. . .", Biochem. Pharmacol., 46, 2229–2234 (1993).
Jackman et al., "The Biochemical Pharmacology of the thymidylate synthase inhibitor. . .", Biochem, Pharmacol., 42, 1885–1895 (1991).

*Primary Examiner*—Mukund J. Shah
*Assistant Examiner*—Matthew V. Grumbling
*Attorney, Agent, or Firm*—Nixon & Vanderhye

[57] ABSTRACT

Quinazolines of the formula

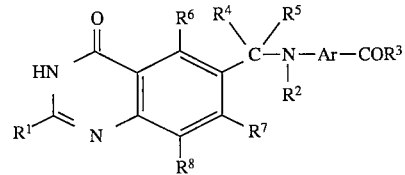

wherein $R^1$ is typically methyl, hydrogen or amino; $R^2$ is typically methyl or propargyl; Ar is typically phenylene or 2'-fluorophenylene; $R^3$ is the residue of a dipeptide substituted, typically by methyl, at position (a), (b) or (c), shown in the following partial formula:

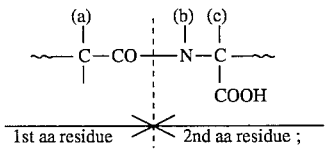

$R^4$, $R^5$, $R^6$ and $R^8$ are typically hydrogen, $R^7$ is typically hydrogen or methyl; or a pharmaceutically acceptable salt, ester or amide thereof are of value in the treatment of cancer.

17 Claims, No Drawings

THYMIDYLATE SYNTHASE INHIBITING QUINAZOLINONES

This is a national stage application, filed under 35 U.S.C. §371, of PCT/GB93/00540, filed Mar. 16, 1993, published as WO93/19051 Sep. 30, 1993.

This invention relates to novel anti-cancer agents and more particularly it relates to quinazoline derivatives which possess anti-cancer activity.

One group of anti-cancer agents comprises antimetabolites having anti-folate activity, such as aminopterin and methotrexate. A newer compound of this type which showed considerable promise in clinical trials is known as CB3717 and is described and claimed in United Kingdom Patent No. 2 065 653B. Despite its promising activity against human breast, ovarian and liver cancer, however, CB3717 shows symptoms of toxicity in humans, particularly in relation to the liver and kidneys. Such adverse side effects are reduced in compounds in which the 2-amino substituent of CB3717 is either missing or is replaced by one of various alternative substituents as described and claimed respectively in United Kingdom Patents Nos. 2 175 903 and 2 188 319.

Compounds of this type are believed to act as anti-cancer agents by inhibiting the enzyme thymidylate synthase which catalyses the methylation of deoxyuridine monophosphate to produce thymidine monophosphate which is required for DNA synthesis. The anti-cancer activity of CB3717 and like compounds may be assessed in vitro by determining their inhibitory effect on that enzyme, and in cell cultures by their inhibitory effect on cancer cell lines such as the mouse lymphoma cell line L1210 and the human breast cancer cell line MCF-7.

Antimetabolites such as aminopterin and methotrexate which are inhibitors of enzymes which utilise folic acid derivatives have also shown promise in the treatment of various allergic diseases such as allergic rhinitis, atopic dermatitis and psoriasis.

We have now found that certain quinazoline derivatives not only show a good level of activity, in particular in respect of their ability to inhibit thymidylate synthase, but also have a different mode of action from CB3717 and other related quinazoline derivatives which have been described. Thus it is believed that CB3717 and more particularly its 2-methyl analogue, which is described and claimed in UK Patent No. 2 188 319, owe anti-tumour activity to an intracellular polyglutamate form but that the compounds of the present invention act directly without undergoing a significant degree of gamma-glutamylation. This alternative mode of action of the compounds of the present invention provides the potential for more precise control in the administration of the compounds to cancer patients, deriving especially from a shorter period of intracellular retention following the completion of administration and a lack of dependence on polyglutamylation which may vary in degree from one patient to another. Moreover, the replacement of the L-glutamic acid residue of CB3717 by an alternative group in the compounds of the present invention will confer different physical properties thereby influencing the overall characteristics of the compounds.

Accordingly the present invention comprises a quinazoline of formula (I):

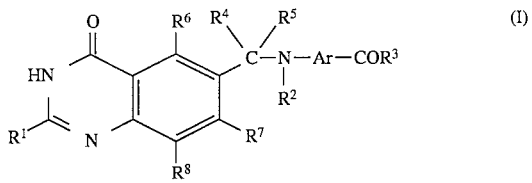

wherein $R^1$ is hydrogen or amino;
or $R^1$ is alkyl, alkoxy or alkylthio each of up to 6 carbon atoms;
or $R^1$ is aryl or aryloxy, each of up to 10 carbon atoms;
or $R^1$ is halogeno, hydroxy or mercapto;
or $R^1$ is alkyl of up to 3 carbon atoms which bears one or more substituents selected from halogeno, hydroxy and alkanoylamino each of up to 6 carbon atoms;
or $R^1$ is alkoxy of up to 3 carbon atoms which bears one or more substituents selected from hydroxy and alkoxy of up to 6 carbon atoms;
wherein $R^2$ is hydrogen or alkyl, alkenyl, alkynyl, hydroxyalkyl, alkoxyalkyl, mercaptoalkyl, alkylthioalkyl, halogenoalkyl, cyanoalkyl, aminoalkyl, alkylaminoalkyl, dialkylaminoalkyl, alkanoylalkyl, carboxyalkyl, carbamoylalkyl or alkanoyl each of up to 6 carbon atoms;
wherein Ar is phenylene or heterocyclene which is unsubstituted or which bears one or more substituents selected from halogeno, cyano, nitro, hydroxy, amino and carbamoyl and alkyl, alkoxy, halogenoalkyl, alkanoylamino and alkoxycarbonyl each of up to 6 carbon atoms;
wherein $R^3$ is the residue of a dipeptide in which the first, N-terminal amino acid residue thereof attached to the carbonyl group of $COR^3$ is an amino acid residue

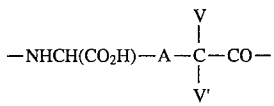

in which A is a carbon-carbon single bond or an alkylene group of up to 5 carbon atoms and V and V' are each separately hydrogen, or alkyl, alkenyl or alkynyl each of up to 6 carbon atoms; and the second amino acid residue is of an α-amino acid but with one or more of the following provisos:
(a) at least one of V and V' is other than hydrogen,
(b) the nitrogen atom of the second amino acid residue is substituted by an alkyl, alkenyl or alkynyl group of up to 4 carbon atoms, by an alkyl group of up to 3 carbon atoms which bears one or more halogeno group substituents or a hydroxy group substituent, or by an ethylene, trimethylene or tetramethylene group linked to the α-carbon atom of the second amino acid residue, and
(c) the α-carbon atom of the second amino acid residue is fully substituted;
wherein $R^4$ is hydrogen or alkyl of up to 4 carbon atoms;
wherein $R^5$ is hydrogen or alkyl of up to 4 carbon atoms; and
wherein each of $R^6$, $R^7$ and $R^8$ is hydrogen or alkyl or alkoxy each of up to 4 carbon atoms; or is halogeno; the quinazoline optionally being in the form of a pharmaceutically acceptable salt, ester or amide thereof.

By way of contrast with the corresponding dipeptides of the L,L configuration which are not one of: (a) substituted on the carbon atom in the first amino acid residue adjacent to the amide linkage between the two residues, (b) N-substituted in the second amino acid residue and (c) fully substituted at the α-carbon atom in the second amino acid residue, the quinazoline dipeptides of the present invention show a resistance to cleavage of the central amide bond of the dipeptide in vivo. Thus, the existence of one or more of these three forms of substitution adjacent to the amide linkage leads to such a resistance to cleavage. Without limitation to any specific theory, it is believed that the type of substitution which is present in a quinazoline of the invention adjacent to the amide linkage between the two residues of the dipeptide achieves this effect through steric hindrance about that linkage.

Although each of the forms of substitution may be present in the compounds of the present invention, it is preferred that no more than two of the forms and particularly only one is present, substitution on the nitrogen atom of the second amino acid residue being of most interest. In a preferred aspect of the invention, therefore, $R^3$ is the residue of a dipeptide in which the first, N-terminal amino acid residue thereof attached to the carbonyl group of $COR^3$ is an amino acid residue

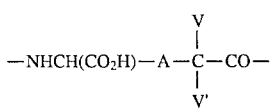

in which A is a carbon-carbon single bond or an alkylene group of up to 5 carbon atoms and V and V' are each separately hydrogen, or alkyl, alkenyl or alkynyl each of up to 6 carbon atoms; and the second amino acid residue is of an α-amino acid substituted on the nitrogen atom by an alkyl, alkenyl or alkynyl group of up to 4 carbon atoms, by an alkyl group of up to 3 carbon atoms which bears one or more halogeno group substituents or a hydroxy group substituent, or by an ethylene, trimethylene or tetramethylene group linked to the α-carbon atom thereof, for example being the residue of an α-amino acid as described hereinafter.

In this specification the terms alkyl, alkenyl, alkynyl and alkylene include both straight and branched chain groups but references to individual alkyl or alkylene groups such as "propyl" or "propylene" are specific for the straight chain group only. An analogous convention applies to other generic terms. Moreover, the numbering system used for the quinazoline nucleus is the conventional one as shown below.

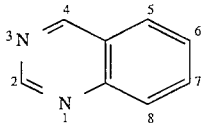

The amino-acid residues are designated in the standard manner (Pure and Applied Chemistry, 1974, 40, 317 and European Journal of Biochemistry, 1984, 138, 9). For the avoidance of doubt, however, it should be noted that γ-glutamyl denotes the radical $H_2NCH(CO_2H)CH_2CH_2CO—$ or $—NHCH(CO_2H)CH_2CH_2CO—$ according to the context, the carbon atoms in these radicals being numbered from the carbon atom of the α-carboxy group as position 1.

It will be observed that a quinazoline of the invention contains at least one asymmetric carbon atom (present in the peptide residue $R^3$) and can therefore exist in optically active forms. It is to be understood that this invention encompasses the various optically active forms of the quinazoline, it being a matter of common general knowledge how such optically active forms may be obtained by stereospecific synthesis or by separation of a mixture of isomeric compounds. One isomer may however be of more interest than another due to the nature of the activity which it exhibits or due to superior physical properties, for example aqueous solubility.

A suitable value for any of $R^1$, $R^2$, $R^4$, $R^5$, $R^6$, $R^7$ or $R^8$ when it is alkyl, or for an alkyl substituent in Ar is, for example, methyl, ethyl, propyl or isopropyl.

A suitable value for $R^2$ when it is alkenyl is, for example, prop-2-enyl, but-2-enyl, but-3-enyl, 2-methylprop-2-enyl, hex-2-enyl, hex-5-enyl or 2,3-dimethylbut-2-enyl.

A suitable value for $R^2$ when it is alkynyl is, for example, prop-2-ynyl, but-2-ynyl, but-3-ynyl, pent-2-ynyl, 3-methylpent-4-ynyl, hex-2-ynyl or hex-5-ynyl.

A suitable value for any of $R^1$, $R^6$, $R^7$ or $R^8$ when it is alkoxy, or for an alkoxy substituent in Ar is, for example, methoxy, ethoxy or isopropoxy.

A suitable value for $R^1$ when it is alkylthio is, for example, methylthio or isopropylthio.

A suitable value for $R^1$ when it is aryl is, for example, phenyl or tolyl.

A suitable value for $R^1$ when it is aryloxy is, for example, phenoxy or tolyloxy.

A suitable value for any of $R^1$, $R^6$, $R^7$ or $R^8$ when it is halogeno is, for example, fluoro, chloro, bromo or iodo.

A suitable value for $R^1$ when it is substituted alkyl is, for example, fluoromethyl, difluoromethyl, trifluoromethyl, 2-fluoroethyl, 3-fluoropropyl, chloromethyl, dichloromethyl, hydroxymethyl, 2-hydroxyethyl, 3-hydroxypropyl, acetamidomethyl, 3-acetamidopropyl or propionamidomethyl.

A suitable value for $R^1$ when it is substituted alkoxy is, for example, 2-hydroxyethoxy, 4-hydroxybutoxy, 3-hydroxy-2-methylpropoxy, 2-methoxyethoxy, 3-methoxypropoxy or 2-ethoxyethoxy.

A suitable value for $R^2$ when it is hydroxyalkyl, alkoxyalkyl, mercaptoalkyl or alkylthioalkyl is, for example 2-hydroxyethyl, 3-hydroxypropyl, 2-methoxyethyl, 2-ethoxyethyl, 3-methoxypropyl, 2-methoxypropyl, 2-mercaptoethyl, 3-mercaptopropyl, 2-methylthioethyl, 3-methylthiopropyl or 2-ethylthioethyl.

A suitable value for $R^2$ when it is halogenoalkyl, cyanoalkyl, aminoalkyl, alkylaminoalkyl or dialkylaminoalkyl is, for example, 2-fluoroethyl, 2-chloroethyl, 2-bromoethyl, 3-fluoropropyl, 3-chloropropyl, cyanomethyl, 2-cyanoethyl, 3-cyanopropyl, 2-aminoethyl, 3-aminopropyl, 3-amino-2-methylpropyl, 2-methylaminoethyl, 2-dimethylaminoethyl, 2-ethylaminoethyl, 2-diethylaminoethyl, 3-methylaminopropyl or 3-dimethylaminopropyl.

A suitable value for $R^2$ when it is alkanoylalkyl, carboxyalkyl, carbamoylalkyl or alkanoyl is, for example, acetonyl, 2-acetylethyl, propionylmethyl, 2-propionylethyl, 3-acetylpropyl, 4-acetylbutyl, carboxymethyl, 2-carboxyethyl, carbamoylmethyl, acetyl, propionyl or butyryl.

A suitable value for Ar when it is phenylene is, for example, 1,3— or particularly 1,4-phenylene.

A suitable value for Ar when it is heterocyclene is, for example, a 5-membered or 6-membered aromatic (that is, fully unsaturated) heterocyclene diradical which contains up to 2 heteroatoms selected from the group consisting of oxygen, nitrogen and sulphur, for example thienylene, pyridylene, pyrimidinylene, thiazolylene or oxazolylene. Of particular interest are compounds in which Ar is pyrimidinylene, particularly pyridylene or especially phenylene.

A suitable halogeno, halogenoalkyl, alkanoylamino or alkoxycarbonyl substituent in Ar is, for example, fluoro, chloro, bromo, iodo, fluoromethyl, difluoromethyl, trifluoromethyl, acetamido, propionamido, isopropionamido, methoxycarbonyl, ethoxycarbonyl or isobutoxycarbonyl.

A suitable level of substitution in Ar, where substitution is present, is three substituents, particularly two substituents or especially one substituent; and one or two substituents may conveniently be at positions adjacent to the atom bonded to the group —COR$^3$, halogeno substituents such as fluoro being preferred.

The first amino acid residue of R$^3$ is and the second amino acid residue of R$^3$ may be of an α-amino acid in which the α-carbon atom is asymmetric, i.e. this carbon atom is bonded to four groups or atoms which differ from each other, one of which is a carboxy group and another of which contains a grouping

bonded to the carbon atom. In the case where the second amino acid residue has an α-carbon atom which is fully substituted none of the four bonds to the α-carbon atom joins it to a hydrogen atom, although two of the substituents may be identical so that the α-carbon atom is not asymmetric.

The first amino acid residue of the peptide residue R$^3$ may be of the L— or D-configuration at its asymmetric α-carbon atom and the second amino acid residue may similarly be of either configuration at its α-carbon atom when that is asymmetric. Conveniently, however, it is preferred that the first amino acid residue, and the second amino acid residue also where appropriate, is of the L-configuration. It will be appreciated that when both V and V' are other than hydrogen but are different groups then the carbon atom to which they are attached will also be asymmetric, giving rise to erythro and threo forms for the amino acid providing the first residue, both of which can exist as optically active isomers.

Although the compounds of the present invention can exist as a mixture of stereoisomers it is preferred that they are resolved into one optically active isomeric form. Such a requirement complicates the synthesis of the compounds and it is preferred therefore that they contain as few asymmetric carbon atoms as possible consistent with achieving the desired activity. Thus, for example, when one of V and V' is other than hydrogen, the presence of an additional asymmetric carbon atom will be avoided if both V and V' are other than hydrogen and are identical groups. In many cases, however, there will be two asymmetric carbon atoms in R$^3$, as discussed hereinbefore, and the preferred L,L-quinazoline dipeptide is conveniently substantially free from the D,D-dipeptide, and conveniently it is also substantially free from the L,D and D,L-dipeptides. In its preferred form, therefore, the dipeptide is substantially free of all of the other three isomeric forms. The term "substantially free" is used herein to indicate the presence of no more than 20% and especially no more than 10% by weight of the other isomer or isomers referred to.

A suitable value for R$^3$ is a dipeptide residue in which the first, N-terminal amino acid residue

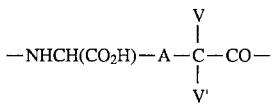

is linked to a second amino acid residue

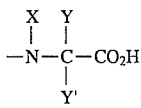

to provide a group R$^3$ of the formula

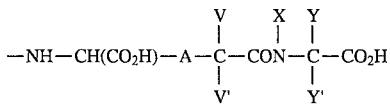

in which A, V and V' are as defined hereinbefore;
  X is hydrogen, an alkyl, alkenyl or alkynyl group of up to 4 carbon atoms or a C$_{1-3}$ alkyl group substituted by one or more halogeno groups or a hydroxy group;
  Y is hydrogen or alkyl, alkenyl or alkynyl each of up to 6 carbon atoms;
  or X and Y together are a group (CH$_2$)$_n$ where n is 2, 3 or 4;
  and Y' is hydrogen or alkyl, alkenyl or alkynyl each of up to 6 carbon atoms;
  or Y' is alkyl of up to 6 carbon atoms which bears one or more substituents selected from amino, carboxy, hydroxy and mercapto;
  or Y' is phenyl or benzyl; but with the proviso that one or more of the following is the case:
    (a) at least one of V and V' is other than hydrogen,
    (b) X is other than hydrogen, and
    (c) Y and Y' are each other than hydrogen.

An alternative value for R$^3$ is a dipeptide residue in which the first, N-terminal amino acid residue

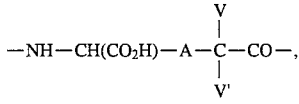

A, V and V' being as defined hereinbefore, is linked to a second amino acid residue which is other than those of the type —N(X)C(Y)(Y')—CO$_2$H described hereinbefore and which corresponds to the residue of a naturally occurring amino acid or such an amino acid which is N-substituted by an alkyl, alkenyl or alkynyl group of up to 4 carbon atoms, or by a C$_{1-3}$ alkyl group substituted by one or more halogeno groups or a hydroxy group.

A suitable value for A is a carbon-carbon single bond or preferably an alkylene group of 2 carbon atoms or particularly 1 carbon atom, for example CH$_2$CH$_2$ and especially CH$_2$.

A suitable value for V or V' when it is alkyl, alkenyl or alkynyl is as described hereinbefore for such groups R$^2$ but especially methyl.

It is preferred that when V is other than hydrogen V' is also other than hydrogen, conveniently being the same as V. One group of compounds of particular interest contains a grouping A—CV(V') in which V and V' are each hydrogen and another group of compounds of some interest contains a grouping A—CV(V') in which V and V' are each the same alkyl group, particularly a methyl group. Hence, in many compounds the grouping A—CV(V') may conveniently be a group A' which is an alkylene group of up to 6 carbon atoms, for example of 1, 3 or particularly 2 carbon atoms, for example $CH_2$, $CH_2CH_2CH_2$ and especially $CH_2CH_2$ or, particularly when the nitrogen atom of the second amino acid residue is not substituted, $CH_2CH(CH_3)$ and especially $CH_2C(CH_3)_2$.

A suitable value for X when it is alkyl, alkenyl or alkynyl of up to 4 carbon atoms is as described hereinbefore for such groups $R^2$, particularly prop-2-enyl, prop-2-ynyl and especially the $C_{1-3}$ alkyl groups such as ethyl and particularly methyl. A suitable value for X when it is a halogeno substituted or hydroxy substituted $C_{1-3}$ alkyl group is as described hereinbefore for such groups $R^1$ the halogeno substituents of choice being fluoro groups with 2-substituted ethyl groups being of particular interest in the case of hydroxy substitution and substituted ethyl and especially methyl groups being of particular interest in the case of halogeno substitution. X is preferably a group other than hydrogen and this may conveniently be one of the monovalent aliphatic hydrocarbon groups as just described or to a lesser extent, together with Y, a group $(CH_2)_n$ where n is 2, 4 or especially 3.

A suitable value for either of Y and Y' when it is alkyl is as described hereinbefore for such groups $R^1$, i.e. propyl and isopropyl, ethyl, and especially methyl.

A suitable value for either of Y and Y' when it is alkenyl or alkynyl is as described hereinbefore for such groups $R^2$ but particularly prop-2-enyl and prop-2-ynyl.

A suitable value for Y' when it is a substituted alkyl group is a group which carries one substituent only, particularly a carboxy group, with that substituent conveniently being on a terminal carbon atom of the alkyl group. Such groups are of particular interest among the various possibilities for Y'. Of especial interest are alkyl groups of up to 3 carbon atoms, i.e. methyl, ethyl, propyl and isopropyl, although larger groups can be of interest, particularly when branched. Preferred groups Y' of this type are thus $CH_2CO_2H$ or $CH_2CH_2CH_2CO_2H$, particularly $CH_2CH(CH_3)CO_2H$ or $CH(CH_3)CH_2CO_2H$ and especially $CH_2CH_2CO_2H$.

Examples of naturally occurring amino acids $H_2NCH(Y')CO_2H$ containing a group Y' which may be present in the group $R^3$ of the quinazolines of the present invention either as such or in N-substituted, for example N-methyl substituted, form (these groups Y' being either a group as specifically discussed above or other forms of group) are alanine (Y'=$CH_3$), arginine (Y'=$(CH_2)_3NHC(NH_2)=NH$), aspartic acid (Y'=$CH_2CO_2H$), cysteine (Y'=$CH_2SH$), glutamic acid (Y'=$CH_2CH_2CO_2H$), isoleucine (Y'=$CH(CH_3)CH_2CH_3$), leucine (Y'=$CH_2CH(CH_3)CH_3$), ornithine (Y'=$(CH_2)_3NH_2$), phenylalanine (Y'=$CH_2C_6H_5$), serine (Y'=$CH_2OH$) and valine (Y'=$CH(CH_3)_2$).

Examples of amino acids $H_2NCH(Y')CO_2H$ which are not naturally occurring which contain groups Y' that may be present in the group $R^3$ of the compounds of the present invention either as such or in N-substituted, for example N-methyl substituted, form are norvaline (Y'=$CH_2CH_2CH_3$), norleucine (Y'=$(CH_2)_3CH_3$), 2-phenylglycine (Y'=$C_6H_5$) and tert-leucine (Y'=$C(CH_3)_3$).

The most preferred groups $R^3$ contain a second amino acid residue which is N-substituted, particularly N-methyl substituted.

Such groups $R^3$ will therefore often be of the formula

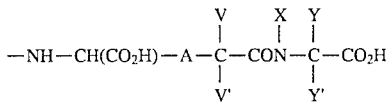

in which A, V, V', X, Y and Y' are as defined hereinbefore but with X being other than hydrogen, particularly being methyl, and preferably with Y being hydrogen and conveniently with V and V' also being hydrogen. Alternatively, somewhat less preferred groups $R^3$ contain a first amino acid residue in which at least one and preferably both of V and V' are other than hydrogen or contain a second amino acid residue in which the α-carbon atom is fully substituted, one of the substituent groups preferably being methyl in each case, both of such possibilities optionally but less preferably being present. Such groups $R^3$ will therefore often be of formula

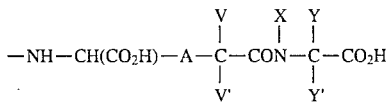

in which A, V, V', X, Y and Y' are as defined hereinbefore but with V and V' each being other than hydrogen, for example each being methyl and/or with Y and Y' each being other than hydrogen, for example each being methyl, and preferably with X being hydrogen.

Groups $R^3$ of particular value have the formula

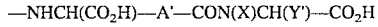

in which A' is an alkylene group of up to 6 carbon atoms, for example being $CH_2CH(CH_3)$, $CH_2C(CH_3)_2$, $CH_2CH_2CH_2$ or $CH_2CH_2$, X is as defined hereinbefore and Y' is methyl, ethyl, propyl, hydroxymethyl, phenyl or benzyl, and especially have the formula

in which A' is as just defined, for example being $CH_2CH(CH_3)$, $CH_2C(CH_3)_2$, particularly $CH_2CH_2CH_2$ and especially $CH_2CH_2$ and m is 1, particularly 3 and especially 2.

Specific examples of $R^3$ are the residues of the dipeptides γ-glutamyl-α-methylalanine, γ-4-methylglutamylglutamic acid, γ-4,4-dimethylglutamylglutamic acid, γ-glutamylproline, γ-glutamyl-N-methylglycine, γ-glutamyl-N-methylalanine, γ-glutamyl-N-methyl-aspartic acid, particularly γ-glutamyl-N-methyl-2-aminoadipic acid and most especially γ-glutamyl-N-methyl-glutamic acid, preferably the L,L forms thereof or the L form in the case of γ-glutamyl-N-methylglycine.

A suitable pharmaceutically-acceptable salt form of a quinazoline of the invention is, for example, an acid addition salt with an inorganic or organic acid, for example hydrochloric, hydrobromic, trifluoroacetic or maleic acid; or an alkali metal, for example sodium, an alkaline earth metal, for example calcium, or ammonium, for example tetra(2-hydroxyethyl)ammonium, salt.

A suitable pharmaceutically-acceptable ester form of a quinazoline of the invention is, for example, an ester with an aliphatic alcohol of up to 6 carbon atoms, for example a methyl, ethyl or tert-butyl ester. A suitable pharmaceutically-acceptable amide form of a quinazoline of the invention is, for example, an unsubstituted amide of the form —$CONH_2$ or particularly a benzyl substituted amide of the form —$CONHCH_2C_6H_5$.

It is to be understood that $R^3$ may contain several carboxy groups. When it comprises three carboxy groups as is the case for various of the preferred dipeptide residues $R^3$, for example when $R^3$ consists of two glutamic acid residues, a salt or ester may be mono-acid-di-salt or -ester or -amide or it may be a di-acid-mono-salt or -ester or -amide or even a tri-salt or -ester or -amide.

Particularly preferred values for the various symbols $R^1$ to $R^8$ and Ar individually are as expressed for the preferred quinazolines described hereinafter. Moreover, in the case of $R^4$, $R^5$, $R^6$ and $R^8$ compounds in which each of these is hydrogen are of especial interest. With $R^7$, however, compounds in which this is other than hydrogen, for example being one of the groups methoxy, fluoro and chloro and particularly an alkyl group such as methyl, are also of especial interest.

A preferred quinazoline of the invention has the formula stated above wherein $R^1$ is halogeno- or hydroxy-substituted alkyl or particularly hydrogen, amino, alkyl or alkoxy, especially fluoromethyl, hydroxymethyl, hydrogen, amino, methyl, ethyl or methoxy;

wherein $R^2$ is methyl, ethyl, prop-2-enyl, prop-2-ynyl, 2-hydroxyethyl, 3-hydroxypropyl, 2-fluoroethyl or acetonyl;

wherein Ar is 1,4-phenylene, 2-fluoro-1,4-phenylene or 2,6-difluoro-1,4-phenylene;

wherein $R^3$ is the residue of the dipeptide γ-glutamyl-N-methyl-2-aminoadipic acid or γ-glutamyl-N-methyl-glutamic acid, preferably in the L,L form;

wherein $R^4$ is hydrogen or methyl;

wherein $R^5$ is hydrogen;

wherein $R^6$ is hydrogen or chloro;

wherein $R^7$ is hydrogen, methyl, fluoro or chloro, and wherein $R^8$ is hydrogen, methoxy or chloro.

An especially preferred quinazoline of the invention has the formula stated above wherein $R^1$ is methyl;

wherein $R^2$ is methyl, ethyl or preferably prop-2-ynyl;

wherein Ar is 1,4-phenylene or 2-fluoro-1,4-phenylene;

wherein $R^3$ is γ-L-glutamyl-N-methyl-L-glutamic acid;

wherein $R^4$ is hydrogen or methyl;

wherein $R^5$ is hydrogen;

wherein $R^6$ is hydrogen or chloro;

wherein $R^7$ is hydrogen, methyl, methoxy, fluoro or chloro and wherein $R^8$ is hydrogen, methyl, methoxy or chloro.

Other quinazolines of the invention of particular interest have the values of $R^1$, $R^2$, $R^4$ to $R^8$ and Ar in combination as indicated above but with $R^3$ having any value as indicated hereinbefore. However, specific particularly preferred quinazolines of the invention are:

N-p-[N-(3,4-dihydro-2-amino-4 -oxoquinazolin-6-yl methyl)-N-methylamino]benzoyl-L-γ-glutamyl-N-methyl-L-glutamic acid, N-p-[N-(3,4-dihydro-2-amino- 4-oxoquinazolin-6-ylm-ethyl)-N-ethylamino]benzoyl-L-γ-glutamyl-N-methyl-L-glutamic acid, N-p-[N-(3,4-dihydro-2-amino-4-oxoquinazolin- 6-ylm-ethyl)-N-(prop-2-ynyl)amino]benzoyl-L-γ-glutamyl-N-methyl-L-glutamic acid, N-p-[N-(3,4-dihydro-2-methyl-4-oxoquinazolin-6 -ylm-ethyl)-N-methylamino]benzoyl-L-δ-glutamyl-N-methyl-L-glutamic acid, N-p-[N-(3,4-dihydro-2-methyl-4 -oxoquinazolin-6-ylm-ethyl)-N-ethylamino]benzoyl-L-γ-glutamyl-N-methyl-L-glutamic acid, N-p-[N-(3,4-dihydro-2-methyl-4 -oxoquinazolin-6-ylm-ethyl)-N-(prop- 2-ynyl)amino]benzoyl-L-γ-glutamyl-N-methyl-L-glutamic acid, N-p-[N-(3,4-dihydro-2,7-dimethyl-4 -oxoquinazolin-6-ylm-ethyl)-N-methylamino]benzoyl-L-γ-glutamyl-N-methyl-L-glutamic acid, N-p-[N-(3,4-dihydro-2,7-dimethyl- 4-oxoquinazolin-6-ylm-ethyl)-N-ethylamino]benzoyl-L-γ-glutamyl-N-methyl-L-glutamic acid, N-p-[N-(3,4-dihydro-2,7 -dimethyl-4-oxoquinazolin-6-ylm-ethyl)-N-(prop- 2-ynyl)amino]benzoyl-L-γ-glutamyl-N-methyl-L-glutamic acid, N-p-[N-(3,4-dihydro-2-methoxy-4 -oxoquinazolin-6 -ylm-ethyl)-N-methylamino]benzoyl-L-γ-glutamyl-N-methyl-L-glutamic acid, N-p-[N-(3,4-dihydro-2-methoxy- 4-oxoquinazolin-6-ylm-ethyl)-Nmethylamino]benzoyl-L-γ-glutamyl-N-methyl-L-glutamic acid, N-p-[N-(3,4-dihydro-2-methoxy- 4-oxoquinazolin-6-ylm-ethyl)-N -(prop-2-ynyl)amino]benzoyl-L-γ-glutamyl-N-methyl-L-glutamic acid, N-p-[N-(3,4-dihydro-2-amino- 4-oxoquinazolin-6--ylm-ethyl)-N-methylamino]-o-fluorobenzoyl-L-γ-glutamyl-N-methyl-L-glutamic acid, N-p-[N-(3,4-dihydro-2-amino-4-oxoquinazolin-6 -ylm-ethyl)-N-ethylamino]-o-fluorobenzoyl-L-γ-glutamyl-N-methyl-L-glutamic acid, N-p-[N-(3,4-dihydro-2-amino-4 -oxoquinazolin-6-ylm-ethyl)-N-(prop- 2-ynyl)amino]-o-fluorobenzoyl-L-γ-glutamyl-N-methyl-L-glutamic acid, N-p-[N-(3,4-dihydro-2-methyl-4-oxoquinazolin- 6-ylm-ethyl)-N-ethylamino]-o-fluorobenzoyl-L-γ-glutamyl-N-methyl-L-glutamic acid, N-p-[N-(3,4-dihydro-2-methyl-4 -oxoquinazolin-6-ylm-ethyl)-Nmethylamino]-o-fluorobenzoyl-L-γ-glutamyl-N-methyl-L-glutamic acid, N-p-[N-(3,4-dihydro-2 -methyl-4-oxoquinazolin-6-ylmethyl)-N-(prop- 2-ynyl)amino]-o-fluorobenzoyl-L-γ-glutamyl-N-methyl-L-glutamic acid, N-p-[N-(3,4-dihydro-2,7-dimethyl-4-oxoquinazolin-6 -ylm-ethyl)-N-methylamino]-o-fluorobenzoyl-L-γ-glutamyl-N-methyl-L-glutamic acid, N-p-[N-(3,4-dihydro-2,7-dimethyl-4-oxoquinazolin-6-ylmethyl)-N-ethylamino]-o-fluorobenzoyl-L-γ-glutamyl-N-methyl-L-glutamic acid, N-p-[N-(3,4-dihydro-2,7-dimethyl- 4-oxoquinazolin-6-ylm-ethyl)-N-(prop- 2-ynyl)amino]-o-fluorobenzoyl-L-γ-glutamyl-N-methyl-L-glutamic acid, N-p-[N-(3,4-dihydro-2-methoxy- 4-oxoquinazolin-6-ylm-ethyl)-N-methylamino]-o-fluorobenzoyl-L-γ-glutamyl-N-methyl-L-glutamic acid, N-p-[N-(3,4-dihydro-2-methoxy-4 -oxoquinazolin-6-ylm-ethyl)-N-ethylamino]-o-fluorobenzoyl-L-γ-glutamyl-N-methyl-L-glutamic acid, and N-p-[N-(3,4-dihydro-2-methoxy-4 -oxoquinazolin-6--ylm-ethyl)-N-(prop-2-ynyl)amino]-o-fluorobenzoyl-L-γ-glutamyl-N-methyl-L-glutamic acid; as well as pharmaceutically acceptable salts, esters and amides thereof.

A quinazoline of the invention may be prepared by any process known to be applicable to the preparation of chemically-related compounds.

The particularly preferred process for the manufacture of a quinazoline of the invention comprises the reaction of an acid of the formula:

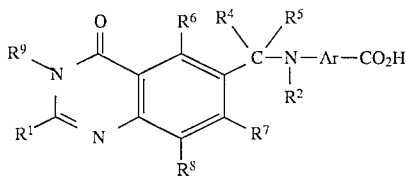

or a reactive derivative thereof, with the terminal amino group of a dipeptide of the formula $R^3$-H wherein $R^1$, $R^2$, $R^3$, $R^4$, $R^5$, $R^6$, $R^7$, $R^8$ and Ar have the meanings stated above, any mercapto, amino and alkylamino group in $R^1$, $R^2$, $R^3$ and Ar and any carboxy group in $R^1$, $R^2$ and Ar is protected by a conventional protecting group, and any hydroxy group in $R^1$, $R^2$, $R^3$ and Ar and any carboxy group in $R^3$ may be protected by a conventional protecting group or alternatively such a hydroxy or carboxy group need not be protected; and wherein $R^9$ is hydrogen or a protecting group, whereafter any undesired protecting group including any protecting group $R^9$ is removed by conventional means.

In this process, and the others described hereinafter, the compound $R^3$-H, and also the quinazoline acid where appropriate, conveniently has the stereochemical configuration at the asymmetric carbon atoms therein which is desired in the final quinazoline of formula (I). The reference to the protection of any amino group in $R^3$ does not of course apply to the terminal amino group of the dipeptide $R^3$-H.

A suitable reactive derivative of an acid of the formula given above may be, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol or an alcohol such as 1-hydroxybenzotriazole; the product of the reaction of the acid and a carbodiimide, for example dicyclohexylcarbodiimide; or particularly an acyl azide, for example an azide formed by the reaction of the acid and an azide such as diphenylphosphoryl azide or an acyl phosphonate, for example an acyl phosphonate formed by the reaction of the acid and a phosphonate such as diethylcyano phosphonate or (1H-1,2,3-benzotriazol-1-yloxy)-tris(pyrrolidino)phosphonium hexafluorophosphate.

A suitable protecting group for a hydroxy group is, for example, an esterifying group, for example an acetyl or benzoyl group, which may be removed by hydrolysis with a base, for example sodium hydroxide, or provided that. $R^2$ does not contain an alkenyl or alkynyl group, the protecting group may be, for example, an α-arylalkyl group, for example a benzyl group, which may be removed by hydrogenation over a catalyst, for example palladium-on-charcoal.

A suitable protecting group for an amino group may be, for example, an alkoxycarbonyl group. for example a tertbutyloxycarbonyl group which may be removed by treatment with an organic acid, for example trifluoroacetic acid; or it may be, for example, a benzyloxycarbonyl group or a trityl group which may be removed by catalytic hydrogenation.

A suitable alternative protecting group for a primary amino group is, for example, a phthaloyl group which may be removed by treatment with an alkylamine, for example dimethylaminopropylamine or with hydrazine.

A suitable protecting group for a carboxy group may be an esterifying group, such as a tert-butyl group which may be removed by treatment with an organic acid, for example trifluoroacetic acid, thereby avoiding the possibility of racemization which can arise with groups removable by base, although the use of a methyl group which may be removed by treatment with a base, for example sodium hydroxide, can be suitable in some cases.

A suitable alternative protecting group for a carboxy group is, for example, an allyl group which may be removed using catalytic amounts of tetrakis triphenylphosphine palladium(O) in the presence of an excess of pyrrolidine.

A suitable protecting group for a mercapto group is, for example, an esterifying group, for example an acetyl group, which may be removed by hydrolysis with a base, for example sodium hydroxide.

$R^9$ is preferably hydrogen rather than a protecting group but a suitable value for $R^9$ when it is a protecting group is, for example, a pivaloyloxymethyl group. Such a group may be removed by hydrolysis with a base, for example sodium hydroxide, but care should be taken to avoid racemization.

The protecting groups for the various carboxy groups in $R^3$ may be esterifying groups such as permit the product after removal of any undesired protecting group in $R^1$, $R^2$, $R^3$ and Ar and of any protecting group $R^9$ to fall within the definition of a quinazoline of the invention. In such instance the esterified carboxy groups in $R^3$ may if desired be retained in the final product. Alternatively a different protecting group may be used in $R^3$ which will be removed.

The dipeptide compound of the formula $R^3$-H may be obtained by any of the various general methods of peptide synthesis which are described in the literature of peptide chemistry. Classical methods involving reaction in solution or solid phase methods may both be used. Preferably, however, the peptide $R^3$-H is prepared by reaction of the appropriate two amino acids in solution, the amino group of the acid providing the N-terminal residue of $R^3$-H and the carboxy group of the acid providing the C-terminal residue of $R^3$-H being protected, for example by protecting groups as described hereinbefore, particularly suitable groups being a benzyloxycarbonyl or trityl group and a tert-butyl or allyl esterifying group, respectively. Although the amino protecting group of the dipeptide will necessarily be removed before reaction of $R^3$-H with the quinazoline carboxylic acid it may be convenient to retain the carboxy protecting group which is already present in the dipeptide.

The carboxylic acid used as starting material may be obtained by the reaction of a compound of the formula:

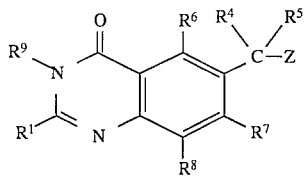

wherein $R^1$, $R^4$, $R^5$, $R^6$, $R^7$, $R^8$ and $R^9$ have the meanings stated above, and Z is a displaceable group, with a compound of the formula:

wherein $R^2$ and Ar have the meanings stated above and $R^{10}$ is a protecting group which can be removed to provide a carboxylic acid.

Z may be, for example, a halogeno or sulphonyloxy group, for example a chloro, bromo, methanesulphonyloxy or toluene-p-sulphonyloxy group.

$R^{10}$ may be, for example, a methyl or an ethyl group which may be removed by hydrolysis with a base, for example sodium hydroxide or $R^{10}$ may be, for example, a tert-butyl group which may be removed by cleavage with an organic acid, for example trifluoroacetic acid.

The protecting group for the carboxy group in $R^{10}$ may be, for example, an esterifying group which can be removed while the protecting group for any mercapto, amino, carboxy and hydroxy group in $R^1$, $R^2$ and Ar is retained.

An alternative procedure for the preparation of the carboxylic acid starting material involves the use of carboxypeptidase G2 enzyme to remove the L-glutamic acid residue from a compound of formula (I) but in which $R^3$ is instead such a residue.

A further preferred process for the manufacture of a quinazoline of the invention, wherein $R^1$ is alkoxy, aryloxy or alkoxy of up to 3 carbon atoms which bears one or more substituents selected from hydroxy and alkoxy of up to 6 carbon atoms, comprises the reaction of a compound of the formula:

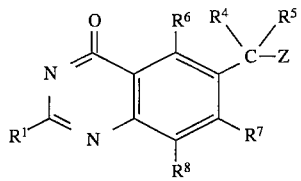

with a compound of the formula:

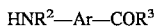

wherein $R^1$ has the last-mentioned meaning stated above; wherein $R^2$, $R^3$, $R^4$, $R^5$, $R^6$, $R^7$, $R^8$ Ar and Z have the meanings stated above, provided that any mercapto, amino, alkylamino and carboxy group in $R^2$, $R^3$ and Ar is protected by a conventional protecting group, for example as stated above, and any hydroxy group in $R^1$, $R^2$, $R^3$ and Ar may be protected by a conventional protecting group, for example as stated above, or alternatively any hydroxy group need not be protected; whereafter any undesired protecting group is removed by conventional means, for example as stated above, and the $R^1$ group situated at the 4-position of the quinazoline ring is cleaved by hydrolysis with a base, for example sodium hydroxide, to form a quinazoline of the invention.

A further preferred process for the manufacture of a quinazoline of the invention, wherein $R^1$ is mercapto or alkylthio comprises the reaction of a quinazoline of the formula:

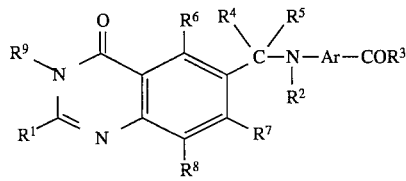

wherein $R^1$ is halogeno or halogenoalkyl and $R^2$, $R^3$, $R^4$, $R^5$, $R^6$, $R^7$, $R^8$, $R^9$ and Ar have the meanings stated above, provided that any mercapto, amino, alkylamino, carboxy and hydroxy group in $R^2$, $R^3$ and Ar may be protected by a conventional protecting group, for example as stated above, or alternatively any amino, alkylamino, carboxy and hydroxy group need not be protected; with thiourea to provide a compound wherein $R^1$ is mercapto; or with an alkyl thiol to provide a compound wherein $R^1$ is alkylthio, arylthio whereafter any undesired protecting group including any protecting group $R^9$ is removed by conventional means, for example as stated above. A further preferred process for the manufacture of a quinazoline of the invention wherein $R^1$ is alkylthio comprises the reaction of a quinazoline of the formula:

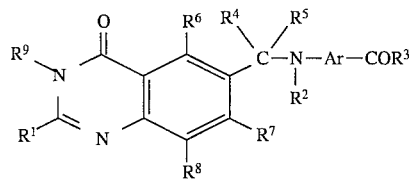

wherein $R^1$ is mercapto and $R^2$, $R^3$, $R^4$, $R^5$, $R^6$, $R^7$, $R^8$, $R^9$ and Ar have the meanings stated above, provided that any mercapto, amino, alkylamino, carboxy and hydroxy group in $R^2$, $R^3$ and Ar may be protected by a conventional protecting group, for example as stated above, or alternatively any amino, alkylamino, carboxy and hydroxy group need not be protected; with a base, for example ammonium hydroxide, followed by alkylation of the resultant thiolate salt with an alkyl halide, for example methyl iodide; whereafter any undesired protecting group including any protecting group $R^9$ is removed by conventional means, for example as stated above.

An alternative process for the manufacture of a quinazoline of the invention comprises the reaction of a compound of the formula:

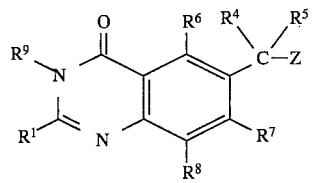

with a compound of the formula:

and within these compounds $R^1$, $R^2$, $R^3$, $R^4$, $R^5$, $R^6$, $R^7$, $R^8$, $R^9$ and Ar have the meanings stated above, provided that when there is a hydroxy group in $R^1$, $R^3$ or Ar, when there is a hydroxyalkyl group in $R^1$ or $R^2$ when there is a hydroxyalkoxy group in $R^1$, when there is an amino group in $R^1$, $R^3$ or Ar, when there is an aminoalkyl group in $R^2$, when there is an alkylaminoalkyl group in $R^2$, when there is a carboxy or carboxyalkyl group in $R^2$ or $R^3$ or when there is a mercapto or mercaptoalkyl group in $R^1$, $R^2$ or $R^3$ any amino, carboxy and mercapto group is protected by a conventional protecting group, for example as stated above, and any hydroxy group may be protected by a conventional protecting group, for example as stated above, or alternatively any hydroxy group need not be protected; Z is a displaceable group; whereafter any undesired protecting group including any protecting group $R^9$ is removed by conventional means, for example as stated above.

When a pharmaceutically acceptable salt of a novel compound of the formula (I) is required, it may be obtained, for example, by reaction of said compound with a suitable acid or base using a conventional procedure. When a pharmaceutically acceptable salt of a novel compound of the formula (I) is required, it may be obtained, for example, by reaction of said compound with a suitable acid or alcohol using a conventional procedure. When a pharmaceutically acceptable salt of a novel compound of the formula (I) is required, it may be obtained, for example, by reaction of said compound or a suitable derivative thereof such as the acid chloride with ammonia or a suitable amine. When an optically active form of a compound of the formula (I) is required, it may be obtained by carrying out one of the aforesaid processes using an optically active starting material, or by resolution of a racemic form of said compound using a conventional procedure.

As stated above quinazolines are believed to function as anti-cancer agents at least in part due to their ability to inhibit the enzyme thymidylate synthase. This anti-cancer activity may be assessed, for example, using one or more of the procedures set out below:

(a) An in vitro assay which determines the ability of a test compound to inhibit the enzyme thymidylate synthase. Thymidylate synthase may be obtained in partially purified form from L1210 mouse leukaemia cells and utilised in the assay using the procedures described by Jackman et al (Cancer Res., 1986, 46, 2810);

(b) An assay which determines the ability of a test compound to inhibit the growth of the leukaemia cell line L1210 in cell culture. The test may be similar to that described in UK Patent Specification No. 2065653B; and (c) An assay which determines the ability of a test compound to inhibit the growth of the human breast cancer cell line MCF-7 in cell culture. The test may be similar to that described by Lippman et al (Cancer Res., 1976, 36, 4595).

Although the pharmacological properties of quinazolines of the invention vary with structural change, in general quinazolines of the invention possess thymidylate synthase inhibitory properties at the following concentrations: $IC_{50}$ in the range, for example, 0.001–10 or 20 µM; or quinazolines of the invention possess L1210 cell-line inhibitory properties at the following concentrations: $IC_{50}$ in the range, for example, 0.001–50 or 100 µM.

In general those quinazolines of the invention which are especially preferred possess thymidylate synthase inhibitory properties at the following concentration: $IC_{50}$ of less than 1 µM; or they possess L1210 cell-line inhibitory properties at the following concentration: $IC_{50}$ of less than 10 µM.

As regards the inhibition of the MCF-7 cancer cell line, in general quinazolines of the invention possess inhibitory properties at the following concentrations: $IC_{50}$ in the range, for example, 0.1–50 or –100 µM. Especially preferred quinazolines possess MCF-7 cell line inhibitory properties at the following concentration: $IC_{50}$ of less than 5 µM.

Thus, by way of example, the quinazoline N-p-[N-(3,4-dihydro-2-methyl-4-oxoquinazolin-6-ylmethyl)-N-(prop-2-ynyl)amino]benzoyl-L-γ-glutamyl-N-methyl-L-glutamic acid, has an $IC_{50}$ of 0.0095 µM against thymidylate synthetase, an $IC_{50}$ of 0.24 µM against the L1210 cell line, an $IC_{50}$ of 0.3 µM against the MCF-7 cell line.

In vivo tests in mice at a dosage of 100 mg/kg with various compounds according to the invention have shown a substantial lack of cleavage of the central amide linkage of the dipeptide as assessed by measurement of the amount of the cleavage product as a percentage of the total of parent compound and cleavage product present in the liver or plasma of a mouse sacrificed 1 hour after intraperitoneal administration of the dipeptide, i.e. cleavage was within the limit of experimental detection which is about 5%. Although a minor degree of cleavage of this amide linkage of the quinazoline is acceptable when it is used in practice, a level of cleavage on administration in vivo of less than 10% is preferred, with no more than about 5% being desirable, especially 2% or 1% or less.

A quinazoline of the invention may be administered to a warm-blooded animal, including a human, in the form of a pharmaceutical composition which comprises the quinazoline in association with a pharmaceutically-acceptable diluent or carrier.

The composition may be in a form suitable for oral administration, as a tablet or capsule, or, especially, for parenteral injection (including intravenous, subcutaneous, intramuscular, intravascular or infusion), as a sterile solution, suspension or emulsion, or for topical administration, as an ointment or cream, or for rectal administration as a suppository.

The composition may contain, in addition to the quinazoline of the invention, one or more other anti-cancer substances selected from, for example, mitotic inhibitors, for example vinblastine; alkylating agents, for example cisplatin, carboplatin and cyclophosphamide; other antimetabolites, for example 5-fluorouracil, cytosine arabinoside and hydroxyurea; intercalating antibiotics, for example adriamycin and bleomycin; enzymes, for example asparaginase; topoisomerase inhibitors, for example etoposide and biological response modifiers, for example interferon.

In general the compositions may be prepared in a conventional manner using conventional excipients.

The quinazoline will normally be administered to a warm-blooded animal at a dose within the range 50–25000 mg per square meter body area of the animal, i.e. approximately 1–500 mg/kg. Where desired, however, dosages outside this range may be employed and, in particular, where the preferred mode of administration involving subcutaneous infusion is used then the does range may be increased to 1–1000 mg/kg. Preferably a daily dose in the range 10–150 mg/kg is employed, particularly 30–80 mg/kg.

Accordingly the present invention also includes a method for aiding regression and palliation of cancer in a patient, particularly a warm-blooded animal such as man, in need of such treatment, which comprises administering to said patient an effective amount of a quinazoline as defined hereinbefore. The invention also provides the use of such a quinazoline in the manufacture of a novel medicament for use in the treatment of cancer.

Quinazolines of the present invention are of interest for a wide range of anti-tumour activities, particularly in the human, including the treatment of breast, ovarian and liver cancer. In addition they are of interest in the context of the treatment of a range of leukaemias, lymphoid malignancies and solid tumours such as carcinomas and sarcomas.

In view of the activity shown by antimetabolites such as aminopterin and methotrexate, which is discussed hereinbefore, the quinazolines of the present invention are also of interest for use in the treament of other conditions, for example allergic conditions such as psoriasis. In using a quinazoline of the invention for such a purpose the compound will normally be administered at a dose within the range 50–25000 mg per square meter body area of the animal, i.e. approximately 1–500 mg/kg. Where desired, however, dosages outside this range may be employed. In general, for the treatment of an allergic condition such as psoriasis topical administration of a quinazoline of the invention is preferred. Thus, for example, for topical administration a daily dose in the range, for example, of 10–150 mg/kg may be used, particularly 30–80 mg/kg.

Compositions containing the quinazolines may be formulated in unit dosage form, i.e. in the form of discrete portions each comprising a unit dose, or a multiple or sub-multiple of a unit dose, for example an amount of the quinazoline in the range of 1–250 or 500 mg.

The invention is illustrated by the following Examples.

The structures of all compounds of the invention were confirmed by proton magnetic resonance and mass spectroscopy and by elemental analysis. Proton magnetic resonance and mass spectra were determined using a Bruker WM250 spectrometer operating at a field strength of 250 MHz. Chemical shifts are reported in parts per million downfield from tetramethylsilane as an internal standard (δ scale) and peak multiplicities are shown thus: s, singlet; d, doublet; d of d's, doublet of doublets; t, triplet; m, multiplet, the attribution believed to be appropriate for each signal also being indicated. Mass spectra were obtained using a VG analytical ZAB SE spectrometer with fast-atom bombardment ionization (FAB) or a Finnigan TSQ 700 spectrometer with electrospray ionization (ESI) or chemical ionization (CI). Where appropriate, either positive ion data or negative ion data were collected.

Column chromatography was performed using Merck Art 15111 silica gel. Petroleum ether refers to the fraction of boiling point 60°–80° C.

Intermediates for the preparation of compounds according to the invention containing other groups $R^1$, $R^2$, $R^4$ to $R^8$ and Ar are described in UK patents 2 065 653, 2 175 903, 2 188 319 and 2 202 847 and in UK patent applications 2 217 709, 2 227 016 and 2 244 708, and in the equivalents thereof filed in other countries.

EXAMPLES

Example 1

N-p-[N-(3,4-Dihydro-2-methyl-4-oxoquinazolin-6-ylmethyl)-N-(prop-2-ynyl)amino]benzoyl-L-γ-glutamyl-N-methyl-L-glutamic acid.

(1) Tri-tert-butyl-L-γ-glutamyl-N-methyl-L-glutamate.

N-Methyl-L-glutamic acid (3.2 g) was added to water (50 ml) and the pH of the solution adjusted to 9 with solid sodium bicarbonate. The solution was cooled to 0° C. and stirred vigorously, while benzyl chloroformate (9 ml) was added dropwise over 20 min. The mixture was stirred for a further 2 h at 0° C. and an additional 2 h at room temperature, then extracted with diethyl ether (2×100 ml). The aqueous solution was then acidified to pH 3 with 5N HCl and the product isolated by extraction with ethyl acetate (2×100 ml). The pooled organic extracts were dried over anhydrous sodium sulphate and the solvent concentrated in vacuo to give a yellow oil, which crystallised on standing. Recrystallisation from water afforded N-(benzyloxycarbonyl)-N-methyl-L-glutamic acid (2.26 g), m.p. 97°–98° C.

NMR Spectrum: (CD$_3$SOCD$_3$, 67° C.) 1.94, 2.14 (2×m, 2H, β-CH$_2$), 2.22 (t, 2H, J=6.27 Hz, γ-CH$_2$), 2.79 (s, 3H, N—CH$_3$), 4.53 (dd, J=5.0, 10.4 Hz, 1H, α-CH), 5.08 (s, 2H, ArCH$_2$), 7.33 (m, 5H, ArH).

Mass Spectrum: (CI) m/e 296 (M+H)$^+$.

Elemental Analysis: Found C, 56.67; H, 5.78; N, 4.72%. C$_{14}$H$_{17}$NO$_6$ requires C, 56.95; H, 5.80; N, 4.74%.

N-(Benzyloxycarbonyl)-N-methyl-L-glutamic acid (1.85 g) was suspended in dichloromethane (52 ml) in a pressure bottle and to this was added concentrated sulphuric acid (0.28 ml). The mixture was cooled to −20° C. and liquid isobutylene (25 ml) added. The stoppered reaction vessel was shaken vigorously at room temperature for 28 hours, then cooled and a saturated solution of sodium bicarbonate (100 ml) and ethyl acetate (200 ml) were added. The organic layer was separated and washed with saturated sodium bicarbonate solution (2×160 ml) and water (100 ml), then dried over anhydrous sodium sulphate, filtered and concentrated in vacuo. The residue was purified by chromatography on a silica gel column using 10% ethyl acetate in dichloromethane as eluant. There was thus obtained di-tert-butyl N-(benzyloxycarbonyl)-N-methyl-L-glutamic acid (1.8 g) as an oil.

NMR Spectrum: (CD$_3$SOCD$_3$, 67° C.) 1.37, 1.38 (2×s, 18H, C(CH$_3$)$_3$), 1.90, 2.07 (2×m, 2H, β-CH$_2$), 2.20 (m, 2H, γ-CH$_2$), 2.79 (s, 3H, N—CH$_3$), 4.44 (dd, J=5.3, 10.2 Hz, 1H, α-CH), 5.11 (m, 2H, ArCH$_2$), 7.33 (m, 5H, ArH).

Mass Spectrum: (CI) m/e 408 (M+H)$^+$.

Elemental Analysis: Found C, 64.74; H, 8.15; N, 3.40%. C$_{22}$H$_{33}$NO$_6$ requires C, 64.84; H, 8.16; N, 3.44%.

A solution of di-tert butyl N-(benzyloxycarbonyl)-N-methyl-L-glutamic acid (1.6 g) in ethyl acetate containing 10% Pd/C (0.22 g) was stirred under hydrogen for 2.5 hours. The catalyst was removed by filtration and the filtrate concentrated to dryness in vacuo, yielding di-tert-butyl N-methyl-L-glutamic acid (1.14 g) as an oil.

NMR Spectrum: (CD$_3$SOCD$_3$) 1.39, 1.42 (2×s, 18H, C(CH$_3$)$_3$), 1.67 (m, 2H, β-CH$_2$), 2.19 (s, 3H, N—CH$_3$), 2.23 (m, 2H, γ-CH$_2$), 2.91 (dd, J=6.1, 7.8 Hz, 1H, α-CH).

Mass spectrum: (CI) m/e 274 (M+H)$^+$.

To a stirred solution of α-tert-butyl-N-benzyloxycarbonyl-L-glutamate (Org. Prep. Proc. Int., 1985, 17, 416; 1.31 g) and N-methylmorpholine (0.37 g) in dry tetrahydrofuran (5 ml) cooled to −20° C. was added isobutyl chloroformate (0.50 g). After 10 minutes a solution of di-tert-butyl N-methyl-L-glutamic acid (1.003 g) in tetrahydrofuran (5 ml) was added. Stirring was continued for 10 minutes at −20° C, and then at laboratory temperature for 4 hours. N-methylmorpholine hydrochloride was filtered off and the filtrate concentrated in vacuo. The residue was purified by chromatography on a silica gel column using a gradient of ethyl acetate in dichloromethane (5–30% v/v) as eluant. The product was triturated in diethyl ether and the white solid isolated by filtration, washed with petrol and dried in vacuo. There was thus obtained tri-tert-butyl N-methyl-[N-(benzyloxy carbonyl)-L-γ-glutamyl]-L-glutamate (1.62 g), m.p. 92°–93° C.

NMR Spectrum: (CD$_3$SOCD$_3$) 1.32, 1.37, 1.38 (3×s, 27H, C(CH$_3$)$_3$), 1.86, 2.03 (2×m, 4H, β-CH$_2$), 2.12, 2.38 (2×m, 4H, γ-CH$_2$), 2.60, 2.79 (2×s, 3H, N—CH$_3$), 3.94 (m, 1H, glu α-CH), 4.49, 4.76 (2×dd, J=4.8, 10.8 Hz, 1H, N—Me glu α-CH), 5.03 (m, 2H, ArCH$_2$), 7.35 (s, 5H, ArH), 7.64 (t, J=7.7 Hz, 1H, NH).

Mass Spectrum: (CI) m/e 593 (M+H)$^+$.

Elemental Analysis: Found C, 62.84; H, 8.16; N, 4.69%. C$_{31}$H$_{48}$N$_2$O$_9$ requires C, 62.82; H, 8.16; N, 4.73%.

A solution of tri-tert-butyl N-methyl-[N-(benzyloxycarbonyl)-L-γ-glutamyl]-L-glutamate (0.80 g) in ethyl acetate containing 10% Pd/C (0.11 g) was stirred under hydrogen for 3 hours. The catalyst was removed by filtration and the filtrate concentrated in vacuo, yielding tri-tert-butyl-L-γ-glutamyl-N-methyl-L-glutamate (0.61 g) as an oil.

NMR Spectrum: (CD$_3$SOCD$_3$) 1.38, 1.39, 1.41, 1.42 (4×s, 27H, C(CH$_3$)$_3$), 1.79, 2.05 (2×m, 4H, β-CH$_2$), 2.12, 2.39 (2×m, 4H, γ-CH$_2$), 2.60, 2.84 (2×s, 3H, N—CH$_3$), 3.18 (dd, J=8.3, 4.9 Hz, 1H, CHNH$_2$), 4.53, 4.78 (2×dd, J=10.5, 4.6 Hz, 1H, N—Me glu α-CH).

Mass Spectrum: (CI) m/e 459 (M+H)$^+$.

(2) N-p-[N-(3,4-Dihydro- 2-methyl-4-oxoquinazolin-6-ylmethyl)-N-(prop- 2-ynyl)amino]benzoic acid A mixture of tert-butyl p-aminobenzoate (Synth. Commun., 1984, 14, 921; 10.5 g), propargyl bromide (7.3 ml of an 80% solution in toluene), potassium carbonate (7.5 g) and N,N-dimethylacetamide (85 ml) was heated to 50° C. for 24 hours, cooled, filtered and evaporated. The residue was purified by chromatography on a silica gel column using a 6:1 v/v mixture of hexane and ethyl acetate as eluant.

A mixture of the product (7.3 g); 6-bromomethyl-3,4-dihydro-2-methylquinazolin- 4-one (8 g; prepared as described in Example 3 of UK Patent 2 188 319B), calcium carbonate (3.2 g) and dimethylformamide (100 ml) was stirred at laboratory temperature for 65 hours, filtered and evaporated. The residue was purified by chromatography on a silica gel column using ethyl acetate as eluant.

The mixture of the product (2.5 g) and trifluoroacetic acid (25 ml) was stirred at laboratory temperature for 10 minutes and evaporated to give the p-aminobenzoic acid as its trifluoroacetic acid salt (2.5 g).

(3) N-p-[N-(3,4-Dihydro-2-methyl-4-oxoquinazolin-6-ylmethyl)-N-(prop- 2-ynyl)amino]benzoyl-L-γ-glutamyl-N-methyl-L-glutamic acid.

A mixture of N-p-[N-(3,4-dihydro-2-methyl-4-oxoquinazolin-6 -ylmethyl)-N-(prop-2-ynyl)amino]benzoic acid, trifluoroacetic acid salt (0.461 g, and tri-tert-butyl-L-γ-glutamyl-N-methyl-L-glutamate (0.60 g) was dissolved in dry dimethylformamide (15 ml) at 0° C. and to this solution was added diethyl cyanophosphonate (0.359 g) and then triethylamine (0.222 g) under a nitrogen atmosphere. The solution was stirred at 0° C. and in the dark for 20 minutes and then at laboratory temperature for 2 hours, then diluted with ethyl acetate (100 ml) and water (100 ml). The water layer was separated and extracted with ethyl acetate (2×100 ml). The combined ethyl acetate extracts were washed with 10% aqueous citric acid (2×50 ml), saturated sodium bicarbonate (100 ml) and dilute aqueous sodium chloride (100 ml), then dried over anhydrous sodium sulphate, filtered and concentrated in vacuo. The residue was purified by chromatography on a silica gel column using ethyl acetate as eluant. The product was precipitated from dichloromethane/petroleum ether and there was thus obtained tri-tert-butyl-N-p-[N-(3,4-dihydro-2-methyl-4 -oxoquinazolin-6-ylmethyl)-N-(prop- 2-ynyl)amino]benzoyl-L-γ-glutamyl-N-methyl-L-glutamate (0.56 g), m.p. 110°–113° C.

NMR Spectrum: (CD$_3$SOCD$_3$) 1.32, 1.33, 1.35, 1.36, 1.39 (5×s, 27H, C(CH$_3$)$_3$), 1.86 (m, 4H, β-CH$_2$), 2.32 (s, 3H, quinazoline 2-CH$_3$), 2.15, 2.44 (2×m, 4H, γ-CH$_2$), 2.61, 2.80 (2×s, 3H, N—CH$_3$), 3.23 (s, 1H, C≡CH), 4.29 (m, 3H, CH$_2$C≡C, glu α-CH), 4.48, 4.77 (2×m, 3H, quinazoline 6-CH$_2$, N—Me glu α-CH), 6.82 (d, J=8.7 Hz, 2H, 3',5'-ArH), 7.54 (d, J=8.4 Hz, 1H, quinazoline 8-H), 7.71 (t, J=8.6 Hz, 3H, quinazoline 7-H, 2',6'—ArH), 7.96 (s, 1H, quinazoline 5-H), 8.28 (t, 1H, glu NH), 12.19 (s, 1H, lactam NH).

Mass Spectrum: (positive ion FAB) m/e 810 (M+Na)$^+$.

Elemental Analysis: Found C, 64.75; H, 7.19; N, 8.73%. C$_{43}$H$_{57}$N$_5$O$_9$.0.5H$_2$O requires C, 64.81; H, 7.33; N, 8.79%.

A mixture of tri-tert-butyl-N-p-[N-(3,4 -dihydro-2-methyl-4-oxoquinazolin-6-ylmethyl)-N-(prop- 2-ynyl)amino]-benzoyl-L-γ-glutamyl-N -methyl-L-glutamate (0.167 g) and trifluoroacetic acid (10 ml) was stirred at laboratory temperature for 1 hour in the dark. The solution was then concentrated in vacuo and the residue triturated with diethyl ether (30 ml). The white solid was isolated by filtration, washed with diethyl ether (4×10 ml) and dried in vacuo. There was thus obtained N-p-[N -(3,4-dihydro-2-methyl-4-oxoquinazolin-6-ylmethyl)-N-(prop-2-ynyl)amino]benzoyl-L-γ-glutamyl-N-methyl-L-glutamic acid, trifluoroacetic acid salt (0.152 g), m.p. 205° C. decomp.

NMR Spectrum: (CD$_3$SOCD$_3$) 1.80–2.14 (m, 4H, β-CH$_2$), 2.42 (s, 3H, quinazoline 2-CH$_3$), 2.14, 2.45 (2×m, 4H, γ-CH$_2$), 2.65, 2.81 (2×s, 3H, N—CH$_3$), 3.24 (s, 1H, C≡CH), 4.35 (s, 3H, CH$_2$C≡C, glu α-CH), 4.81 (s, 2H, quinazoline 6-CH$_2$), 4.58, 4.91 (dd, J=11.0, 4.5 Hz, 1H, N—Me glu α-CH), 6.83 (d, J=8.7 Hz, 2H, 3',5'-ArH) 7.59 (d, J=8.4 Hz, 1H, quinazoline 8-H), 7.75 (m, 3H, 2',6'-ArH, quinazoline 7-H), 8.00 (s, 1H, quinazoline 5-H), 8.32 (d, J=7.3 Hz, 1H, glu NH).

Mass Spectrum: (positive ion FAB) m/e 642 (M+Na)$^+$.

Elemental Analysis: Found C, 52.93; H, 5.18; N, 8.41; F, 7.65%. C$_{31}$H$_{33}$N$_5$O$_9$.1.1CF$_3$COOH.0.5Et$_2$0.1H$_2$O requires C, 52.84; H, 5.18; N, 8.75; F, 7.83%.

Example 2

N-p-[N-(3,4-Dihydro-2-methyl-4-oxoquinazolin-6-ylmethyl)-N-(prop-2-ynyl)amino]-benzoyl-L-γ-glutamyl-N-methylglycine (1) Di-tert-butyl-L-γ-glutamyl-N-methylglycine.

N-methylglycine (7.0 g) was added to water (50 ml) and the pH of the solution adjusted to 9 with solid sodium bicarbonate. The solution was cooled to 0° C. and stirred vigorously, while benzyl chloroformate (19 ml) was added dropwise over 20 minutes. The mixture was stirred for a further 2 hours at 0° C. and an additional 2 hours at room temperature, then extracted with diethyl ether (2×130 ml). The aqueous solution was then acidified to pH 3 with 5N HCl and the product isolated by extraction with ethyl acetate (2×130 ml). The combined organic extracts were dried over anhydrous sodium sulphate and the solution concentrated in vacuo to give N-(benzyloxycarbonyl)-N-methylglycine as a pale yellow oil (16.2 g).

NMR Spectrum: (CD$_3$SOCD$_3$, 72° C.) 2.91 (s, 3H, N—CH$_3$), 3.94 (s, 2H, CH$_2$CO$_2$H), 5.07 (s, 2H, ArCH$_2$), 7.33 (s, 5H, ArH).

Mass Spectrum: (ESI) m/e 223 (M$^+$).

To a stirred solution of N-(benzyloxycarbonyl)-N-methylglycine (7.86 g) and tertiary butyl alcohol (4.68 ml) in chloroform (30 ml) cooled in an ice-water bath was added a solution of dicyclohexylcarbodiimide (8.0 g) in chloroform (30 ml), and then 4-dimethylaminopyridine (0.04 g) as catalyst. Stirring was continued at 0° C. for 2 hours, then the mixture was kept at 4° C. overnight. Dicyclohexylurea was removed by filtration and the solvent concentrated in vacuo. The residue was dissolved in ethyl acetate (110 ml) and acetic acid (1.10 ml) was added. The solution was stored at 4° C. for 2 hours. After filtration, the ethyl acetate was washed with 5% aqueous sodium bicarbonate solution (2×70 ml), water (3×80 ml) and dried over anhydrous magnesium sulphate. The solution was concentrated in vacuo and the residue purified by chromatography on a silica gel column using 30% ethyl acetate in petrol as eluant. There was thus obtained tert-butyl-N-(benzyloxycarbonyl)-N-methylglycine (3.6 g) as an oil.

NMR Spectrum: (CD$_3$SOCD$_3$) 1.36, 1.41 (2×s, 9H, C(CH$_3$)$_3$), 2.88, 2.91 (2×s, 3H, N—CH$_3$), 3.91, 3.94 (2×s, 2H, CH$_2$COOH), 5.05, 5.10 (2×s, 2H, ArCH$_2$), 7.31, 7.36 (2×m, 5H, ArH).

Mass Spectrum: (ESI) m/e 279 (M⁺).

Elemental Analysis: Found C, 64.27; H, 7.62; N, 5.03%. $C_{15}H_{21}NO_4$ requires C, 64.50; H, 7.58; N, 5.01%.

A solution of tert-butyl-N-(benzyloxycarbonyl)-N-methylglycine (1.60 g) in ethyl acetate containing 10% Pd/C (0.23 g) was stirred under hydrogen for 2.5 hours. The catalyst was removed by filtration and the filtrate concentrated in vacuo, yielding tert-butyl-N-methylglycine (0.71 g) as an oil.

NMR Spectrum: (CD₃SOCD₃) 1.41 (s, 9H, C(CH₃)₃), 2.25 (s, 3H, N—CH₃), 3.13 (s, 2H, CH₂).

Mass Spectrum: (CI) m/e 146 (M+H)⁺.

To a stirred solution of α-tert-butyl-N-benzyloxycarbonyl-L-glutamate (1.63 g) and N-methylmorpholine (0.487 g) in dry tetrahydrofuran (8 ml) cooled to −20° C. was added isobutyl chloroformate (0.657 g). After 10 minutes a solution of tert-butyl-N-methylglycine (0.70 g) in tetrahydrofuran (8 ml) was added. Stirring was continued for 10 minutes at −20° C., and then at laboratory temperature for 4 hours. N-methylmorpholine hydrochloride was filtered off and the filtrate concentrated in vacuo. The residue was purified by chromatography on a silica gel column using 5% ethyl acetate in dichloromethane as eluant, affording di-tert-butyl-N-methyl-[N-(benzyloxycarbonyl)-L-γ-glutamyl]glycine as a yellow oil (1.73 g).

NMR Spectrum: (CD₃SOCD₃) 1.32, 1.38, 1.39, 1.41 (4×s, 18H, C(CH₃)₃), 1.77, 1.87 (2×m, 2H, β-CH₂), 2.24, 2.38 (2×m, 2H, γ-CH₂), 2.79, 2.95 (2×s, 3H, N—CH₃), 3.93(m) and 4.08(s) (3H, CH₂CO₂Buᵗ, α-CH), 5.03 (m, 2H, ArCH₂), 7.36 (m, 5H, ArH), 7.64 (t, 1H, NH).

Mass Spectrum: (CI) m/e 465 (M+H)⁺.

Elemental Analysis: Found C, 61.56; H, 7.81; N, 5.97%. $C_{24}H_{36}N_2O_7.0.5H_2O$ requires C, 61.45; H, 7.84; N, 5.97%.

A solution of di-tert-butyl-N-methyl-[N-(benzyloxycarbonyl)-L-γ-glutamyl]glycine (0.80 g) in ethyl acetate containing 10% Pd/C (0.150 g) was stirred under hydrogen for 6 hours. The catalyst was removed by filtration and the filtrate concentrated in vacuo, yielding di-tert-butyl-L-γ-glutamyl-N-methylglycine (0.53 g) as a yellow oil.

NMR Spectrum: (CD₃SOCD₃) 1.40, 1.41, 1.43 (3×s, 18H, C(CH₃)₃), 1.59, 1.77 (2×m, 2H, β-CH₂), 2.24, 2.40 (2×m, 2H, γ-CH₂), 2.79, 2.99 (2×s, 3H, N—CH₃), 3.17 (m, 1H, α-CH), 4.02(s) and 4.10(d) (2H, CH₂CO₂Buᵗ).

Mass Spectrum: (ESI) m/e 331 (M+H)⁺.

(2) N-p-[N-(3,4-Dihydro-2-methyl-4-oxoquinazolin-6-ylmethyl)-N-(prop-2-ynyl)amino]benzoyl-L-γ-glutamyl-N-methylglycine.

A mixture of N-p-[N-(3,4-dihydro-2-methyl-4-oxoquinazolin-6-ylmethyl)-N-(prop-2-ynyl)amino]benzoic acid, trifluoroacetic acid salt (0.553 g) and di-tert-butyl-L-γ-glutamyl-N-methylglycine (0.53 g) was dissolved in dry dimethylformamide (15 ml) at 0° C. and to this solution was added diethyl cyanophosphonate (0.359 g) and then triethylamine (0.222 g) under a nitrogen atmosphere. The solution was stirred at 0° C. and in the dark for 20 minutes and then at laboratory temperature for 3 hours, then diluted with ethyl acetate (100 ml) and water (100 ml). The water layer was separated and extracted with ethyl acetate (2×100 ml). The combined ethyl acetate extracts were washed with 10% aqueous citric acid (2×50 ml), saturated sodium bicarbonate (100 ml) and dilute aqueous sodium chloride (100 ml), then dried over sodium sulphate, filtered and concentrated in vacuo. The residue was purified by chromatography on a silica gel column using ethyl acetate as eluant. The product was precipitated from cold dichloromethane/diethyl ether and there was thus obtained di-tert-butyl-N-p-[N-(3,4-dihydro-2-methyl-4-oxoquinazolin-6-ylmethyl)-N-(prop-2-ynyl)amino]benzoyl-L-γ-glutamyl-N-methylglycine (0.22 g), m.p. 104°–108° C.

NMR Spectrum: (CD₃SOCD₃) 1.30, 1.39 (2×s, 18H, C(CH₃)₃), 2.33 (s, 3H, quinazoline 2-CH₃), 1.96 (m, 2H, β-CH₂), 2.26, 2.45 (2×m, 2H, γ-CH₂), 2.79, 2.95 (2×s, 3H, N—CH₃), 3.23 (s, 1H, C≡CH), 3.95(d) and 4.06(s) (2H, CH₂CO₂), 4.25 (m, 1H, α-CH), 4.33 (s, 2H, CH₂C≡C), 4.77 (s, 2H, quinazoline 6-CH₂), 6.81 (m, 2H, 3',5'-ArH), 7.54 (d, J=8.3 Hz, 1H, quinazoline 8-H), 7.74 (m, 3H, quinazoline 7-H, 2',6'-ArH), 7.96 (s, 1H, quinazoline 5-H), 8.28 (t, 1H, NH), 12.19 (s, 1H, lactam NH).

Mass Spectrum: (positive ion FAB) m/e 682 (M+Na)⁺.

Elemental Analysis: Found C, 65.12; H, 6.86; N, 10.50%. $C_{36}H_{45}N_5O_7.0.25H_2O$ requires C, 65.09; H, 6.90; N, 10.54%.

A mixture of di-tert-butyl-N-p-[N-(3,4-dihydro-2-methyl-4-oxoquinazolin-6-ylmethyl)-N-(prop-2-ynyl)amino]benzoyl-L-γ-glutamyl-N-methylglycine (0.074 g) and trifluoroacetic acid (5 ml) was stirred at laboratory temperature for 1 hour in the dark. The solution was then concentrated in vacuo and the residue triturated with diethyl ether (20 ml). The white solid was isolated by filtration, washed with diethyl ether (4×10 ml) and dried in vacuo. There was thus obtained N-p-[N-(3,4-dihydro-2-methyl-4-oxoquinazolin-6-ylmethyl)-N-(prop-2-ynyl)amino]benzoyl-L-γ-glutamyl-N-methylglycine, trifluoroacetate salt (0.60 g), m.p. 140° C. decomp.

NMR Spectrum: (CD₃SOCD₃) 2.01 (m, 2H, β-CH₂), 2.33, 2.42 (2×m, 2H, γ-CH₂), 2.42 (s, 3H, quinazoline 2-CH₃), 2.81, 2.97 (2×s, 3H, N—CH₃), 3.24 (s, 1H, C≡CH), 3.98 (d, J=8.0 Hz) and 4.10(s) (2H, CH₂CO₂), 4.36 (m, 3H, CH₂C≡C, α-CH), 4.81 (s, 2H, quinazoline 6-CH₂), 6.84 (d, J=8.3 Hz, 2H, 3',5'-ArH), 7.59 (d, J=8.5 Hz, 1H, quinazoline 8-H), 7.76 (m, 3H, quinazoline 7-H, 2',6'-ArH), 8.01 (s, 1H, quinazoline 5-H), 8.33 (t, 1H, NH).

Mass Spectrum: (positive ion FAB) m/e 570 (M+Na)⁺.

Elemental Analysis: C, 53.98; H, 5.63; N, 9.02; F, 8.15%. $C_{28}H_{29}N_5O_7.1.1CF_3COOH0.8H_2O0.8Et_2O$ requires C, 53.72; H, 5.35; N, 9.38; F, 8.39%.

Example 3

N-p-[N-(3,4-Dihydro-2-methyl-4-oxoquinazolin-6-ylmethyl)-N-(prop-2-ynyl)amino]benzoyl-L-γ-glutamyl-L-proline (1) Di-tert-butyl-L-γ-glutamyl-L-proline.

To a stirred solution of α-tert-butyl-N-benzyloxycarbonyl-L-glutamate (3.15 g) and N-methylmorpholine (0.909 g) in dry tetrahydrofuran (10 ml) cooled to −20° C. was added isobutyl chloroformate (1.22 g). After 10 minutes a solution of tert-butyl-L-proline (1.54 g) in tetrahydrofuran (10 ml) was added. Stirring was continued for 10 minutes at −20° C., and then at laboratory temperature for 4 hours. N-methylmorpholine hydrochloride was filtered off and the filtrate concentrated in vacuo. The residue was purified by chromatography on a silica gel column using a gradient of 10% to 30% ethyl acetate in dichloromethane as eluant. The product was triturated in petrol and the white solid isolated by filtration, washed with petrol and dried in vacuo. There was thus obtained di-tert-butyl-N-[N-(benzyloxycarbonyl)-L-γ-glutamyl]-L-proline (2.86 g), m.p. 106°–108° C.

NMR Spectrum: (CD$_3$SOCD$_3$) 1.37, 1.39 (2×s, 18 H, C(CH$_3$)$_3$), 1.62–2.10 (m, 6H, glu β-CH$_2$, proline 3-and 4-CH$_2$), 2.33 (m, 2H, glu γ-CH$_2$), 3.42 (m, 2H, proline 5-CH$_2$), 3.93 (m, 1H, glu α-CH), 4.13, 4.40 (2×dd, J=8.8, 3.9 Hz, 1H, proline 2-CH), 5.03 (m, 2H, ArCH$_2$), 7.35 (m, 5H, ArH), 7.59 (t, 1H, glu NH).

Mass Spectrum: (CI) m/e 491 (M+H)$^+$.

Elemental Analysis: Found C, 63.39; H, 7.78; N, 5.69%. C$_{26}$H$_{38}$N$_2$O$_7$ requires C, 63.65; H, 7.81; N, 5.71%.

A solution of di-tert-butyl-N-[N-(benzyloxycarbonyl)-L-γ-glutamyl]-L-proline (0.98 g) in ethyl acetate containing 10% Pd/C (0.15 g) was stirred under hydrogen for 8 hours. The catalyst was removed by filtration and the filtrate concentrated in vacuo, yielding di-tert-butyl-L-γ-glutamyl-L-proline (0.70 g) as an oil.

NMR Spectrum: (CD$_3$SOCD$_3$) 1.37, 1.40 (2×s, 18H, C(CH$_3$)$_3$), 1.55–2.10 (m, 6H, glu β-CH$_2$, proline 3-and 4-CH$_2$), 2.33 (t, J=7.5 Hz, 2H, γ-CH$_2$), 3.16 (m, 1H, glu α-CH), 3.48 (t, J=6.7 Hz, 2H, proline 5-CH$_2$), 4.14, 4.40 (2×dd, J=8.8, 3.9 Hz, 1H, proline 2-CH).

Mass Spectrum: (CI) m/e 357 (M+H)$^+$.

(2) N-p-N-(3,4-Dihydro-2-methyl-4-oxoquinazolin-6-ylmethyl)-N-(prop-2-ynyl)amino]benzoyl-L-γ-glutamyl-L-proline.

A mixture of N-p-[N-(3,4-dihydro-2-methyl-4-oxoquinazolin-6-ylmethyl)-N-(prop-2-ynyl)amino]benzoic acid, trifluoroacetic acid salt (0.461 g) and di-tert-butyl-L-γ-glutamyl-L-proline (0.524 g) was dissolved in dry dimethylformamide (15 ml) at 0° C. and to this solution was added diethyl cyanophosphonate (0.359 g) and then triethylamine (0.222 g) under a nitrogen atmosphere. The solution was stirred at 0° C. and in the dark for 20 minutes and then at laboratory temperature for 3 hours, then diluted with ethyl acetate (100 ml) and water (100 ml). The water layer was separated and extracted with ethyl acetate (2×100 ml). The combined ethyl acetate extracts were washed with 10% aqueous citric acid (2×50 ml), saturated sodium bicarbonate (100 ml) and dilute aqueous sodium chloride (100 ml), then dried over anhydrous sodium sulphate, filtered and concentrated in vacuo. The residue was purified by chromatography on a silica gel column using ethyl acetate as eluant. The product was precipitated from cold diethyl ether/petrol and there was thus obtained di-tert-butyl-N-p-[N-(3,4-dihydro-2-methyl-4-oxoquinazolin-6-ylmethyl)-N-(prop-2-ynyl)amino]benzoyl-L-γ-glutamyl-L-proline (0.192 g), m.p. 113°–117° C.

NMR Spectrum: (CD$_3$SOCD$_3$) 1.31, 1.35, 1.39 (3×s, 18H, C(CH$_3$)$_3$), 1.70–2.10 (m, 6H, glu β-CH$_2$, proline 3- and 4-CH$_2$), 2.32 (s, 3H, quinazoline 2-CH$_3$), 2.38 (t, J=7.5 Hz, 2H, glu γ-CH$_2$), 3.19 (s, 1H, C≡CH), 3.41 (m, 2H, proline 5-CH$_2$), 4.15, 4.40 (2×dd, J=9.0, 3.8 Hz, 1H, proline 2-CH), 4.32 (m, 3H, CH$_2$C≡C, glu α-CH), 4.77 (s, 2H, quinazoline 6-CH$_2$), 6.83 (d, J=8.9 Hz, 2H, 3',5'-ArH), 7.53 (d, J=8.4 Hz, 1H, quinazoline 8-H), 7.68 (dd, J=8.4 Hz, 2.0 Hz, 1H, quinazoline 7-H), 7.73 (d, J=9.0 Hz, 2H, 2',6'-ArH), 7.97 (d, J=2.0 Hz, 1H, quinazoline 5-H), 8.23 (t, 1H, NH).

Mass Spectrum: (positive ion FAB) m/e 708 (M+Na)$^+$.

Elemental Analysis: Found C, 65.81; H, 6.88; N, 10.00%. C$_{38}$H$_{47}$N$_5$O$_7$.0.5H$_2$O requires C, 65.69; H, 6.96; N, 10.08%.

A mixture of di-tert-butyl-N-p-[N-(3,4-dihydro-2-methyl-4-oxoquinazolin-6-ylmethyl)-N-(prop-2-ynyl) amino] benzoyl-L-γglutamyl-L-proline (0.067 g) and trifluoroacetic acid (5 ml) was stirred at laboratory temperature for 1 hour in the dark. The solution was then concentrated in vacuo and the residue triturated with diethyl ether (20 ml). The white solid was isolated by filtration, washed with diethyl ether (4×10 ml) and dried in vacuo. There was thus obtained N-p-[N-(3,4-dihydro-2-methyl-4-oxoquinazolin-6-ylmethyl)-N-(prop-2-ynyl)amino]benzoyl-L-γ-glutamyl-L-proline, trifluoroacetate salt (0.054 g), m.p. 162° C. decomp.

NMR Spectrum: (CD$_3$SOCD$_3$) 1.84, 2.08 (2×m, 6 H, glu β-CH$_2$, proline 3- and 4-CH$_2$), 2.39 (m, 5H, quinazoline 2-CH$_3$, glu γ-CH$_2$), 3.23 (s, 1H, C≡CH), 3.42 (m, 2H, proline 5-CH$_2$), 4.34 (m, 3H, CH$_2$≡C, glu α-CH), 4.23, 4.48 (dd, J=9.9, 3.5 Hz, 1H, proline 2-CH), 4.80 (s, 2H, quinazoline 6-CH$_2$), 6.83 (d, J=8.8 Hz, 2H, 3',5'-ArH), 7.57 (d, J=8.4 Hz, 1H, quinazoline 8-H), 7.74 (d, J=8.7 Hz, 3H, 2',6'-ArH, quinazoline 7-H), 7.99 (s, 1H, quinazoline 5-H), 8.32 (t, 1H, NH).

Mass Spectrum: (positive ion FAB) m/e 596 (M+Na)$^+$.

Elemental Analysis: Found C, 55.44; H, 4.91; N, 9.81%. C$_{30}$H$_{31}$N$_5$O$_7$.1.1CF$_3$CO$_2$H 0.22Et$_2$O requires C, 55.54; H, 4.83; N, 9.79%.

Example 4

N-p-[N-(3,4-Dihydro-2-methyl-4-oxoquinazolin-6-ylmethyl)-N-(prop-2-ynyl)amino]benzoyl-L-γ-glutamyl-α-methylalanine (1) Di-tert-butyl-L-γ-glutamyl-α-methylalamine.

α-Aminoisobutyric acid (6.18 g), tert-butyl acetate (200 ml) and 70% aqueous perchloric acid (9.45 g) were stirred at laboratory temperature for 7 days. The mixture was then cooled in an ice-water bath and extracted with 0.5N hydrochloric acid (4×50 ml). The combined aqueous extracts were immediately neutralised with solid sodium bicarbonate. The aqueous solution was extracted with diethyl ether (3×100 ml), the ether extracts pooled, dried over anhydrous sodium sulphate and the ether evaporated in vacuo to give tert-butyl α-methylalanine (4.98 g).

NMR Spectrum: (CD$_3$SOCD$_3$) 1.16 (s, 6H, C(CH$_3$)$_2$), 1.40 (s, 9H, C(CH$_3$)$_3$).

To a stirred solution of α-tert-butyl-N-benzyloxycarbonyl-L-glutamate (3.033 g) and N-methylmorpholine (0.909 g) in dry tetrahydrofuran (10 ml) cooled to −20° C. was added isobutyl chloroformate (1.224 g). After 10 minutes a solution of tert-butyl α-methylalanine (2.0 g) in tetrahydrofuran (5 ml) was added. Stirring was continued for 10 minutes at −20° C., and then at laboratory temperature for 1 hour. N-Methylmorpholine hydrochloride was filtered off and the filtrate concentrated in vacuo. The residue was purified by chromatography on a silica gel column using 2% methanol in dichloromethane as eluant. The product was crystallised from diethyl ether/petrol and the white solid isolated by filtration, washed with petrol and dried in vacuo. There was thus obtained di-tert-butyl [N-(benzyloxycarbonyl)-L-γ-glutamyl]-L-α-methylalanine (3.855 g), m.p. 109°–1100° C.

NMR Spectrum: (CD$_3$SOCD$_3$) 1.27 (s, 6H, C(CH$_3$)$_2$), 1.34, 1.39 (2×s, 18H, C(CH$_3$)$_3$), 1.73, 1.90 (2×m, 2H, β-CH$_2$), 2.13 (t, J=7.3 Hz, 2H, γ-CH$_2$), 3.90 (m, 1H, glu α-CH), 5.03 (m, 2H, ArCH$_2$), 7.36 (m, 5H, ArH), 7.64 (d, J=7.5 Hz, 1H, glu NH), 8.06 (s, 1H, α-methylalanine NH).

Mass Spectrum: (positive ion FAB) m/e 501 (M+Na)$^+$.

Elemental Analysis: Found C, 62.73; H, 8.02; N, 5.82%. C$_{25}$H$_{38}$N$_2$O$_7$ Requires: C, 62.74; H, 8.00; N, 5.85%.

A solution of the product (0.669 g) in ethyl acetate containing 10% Pd/C (0.2 g) was stirred under hydrogen for 3 hours. The catalyst was removed by filtration and the filtrate concentrated in vacuo, yielding di-tert-butyl-L-γ-glutamyl-α-methylalanine (0.541 g) as an oil.

(2) N-p-[N-(3,4-Dihydro-2-methyl-4-oxoquinazolin-6-ylmethyl)-N-(prop- 2-ynyl)amino]benzoyl-L-γ-glutamyl-α-methylalanine.

The process described in Example 1(3) was repeated using di-tert-butyl-L-γ-glutamyl-α-methylalanine (0.541 g) as starting material in place of tri-tert-butyl-L-γ-glutamyl-N-methyl-L-glutamate. There was thus obtained di-tert-butyl-N-p-[N-(3,4 -dihydro-2-methyl-4-oxoquinazolin-6-yl-methyl)-N-(prop- 2-ynyl)-amino]benzoyl-L-γ-glutamyl-α-methylalanine (0.486 g), m.p. 115°–116° C.

NMR Spectrum: (CD$_3$SOCD$_3$) 1.26 (s, 6H, C(CH$_3$)$_2$), 1.33, 1.39 (2×s, 18H, C(CH$_3$)$_3$), 1.91, 1.99 (2×m, 2H, β-CH$_2$), 2.14 (m, 2H, γ-CH$_2$), 2.32 (s, 3H, quinazoline 2-CH$_3$), 3.27 (s, 1 H, C≡H), 4.25 (m, 1H, glu α-CH), 4.34 (s, 2H, CH$_2$C≡C), 4.78 (s, 2H, quinazoline 6-CH$_2$), 6.83 (d, J=8.9 Hz, 2H, 3',5'-ArH), 7.54 (d, J=8.4 Hz, 1H, quinazoline 8-H), 7.70 (dd, J=2.0 Hz, 1H, quinazoline 7-H), 7.74 (d, J=8.8 Hz, 2H, 2',6'-ArH), 7.96 (d, J=1.6 Hz, 1H, quinazoline 5-H), 8.07 (s, 1H, α-methylalanine NH), 8.34 (d, J=7.4 Hz, 1H, glu NH), 12.20 (s, 1H, lactam NH).

Mass Spectrum: (positive ion FAB) m/e 674 (M+H)$^+$.

Elemental Analysis: Found C, 65.05; H, 7.04; N, 10.18%. C$_{37}$H$_{47}$N$_5$O$_7$.0.5H$_2$O requires C, 65.08; H, 7.09; N, 10.26%.

Di-tert-butyl-N-p-[N-(3,4-dihydro-2-methyl-4 -oxo-quinazolin-6-ylmethyl)-N-(prop- 2-ynyl)amino]benzoyl-L-γ-glutamyl-α-methylalanine (0.1 g) was treated with trifluoroacetic acid as described in Example 1(3). There was thus obtained N-p-[N-(3,4 -dihydro-2-methyl-4-oxoquinazolin-6-ylmethyl)-N-(prop-2-ynyl)amino]benzoyl-L-γ-glutamyl-α-methylalanine (0.062 g), m.p. 155°–158° C.

NMR Spectrum: (CD$_3$SOCD$_3$) 1.29 (s, 6H, C(CH$_3$)$_2$), 1.89, 2.02 (2×m, 2H, β-CH$_2$), 2.18 (m, 2H, γ-CH$_2$), 2.38 (s, 3H, quinazoline 2-CH$_3$), 3.23 (s, 1H, C≡CH), 4.29 (m, 1H, glu α-CH), 4.34 (s, 2H, CH$_2$C≡C), 4.80 (s, 2H, quinazoline 6-CH$_2$), 6.83 (d, J=8.3 Hz, 2H, 3',5'-ArH), 7.57 (d, J=8.3 Hz, 1H, quinazoline 8-H), 7.75 (d, J=8.1 Hz, 3H, 2',6'-ArH and quinazoline 7-H), 7.98 (s, 1H, quinazoline 5-H), 8.02 (s, 1H, α-methylalanine NH), 8.29 (d, J=7.6 Hz, 1H, glu NH), 12.40 (br, CO$_2$H).

Mass Spectrum: (positive ion FAB) m/e 584 (M+Na)$^+$.

Elemental Analysis: Found C, 55.21; H, 5.00; N, 10.57; F, 5.80%. C$_{29}$H$_{31}$N$_5$O$_7$.0.7CF$_3$CO$_2$H.1H$_2$O requires C, 55.37; H, 5.15; N, 10.62; F, 6.05%.

Example 5

N-p-[N-(3,4-Dihydro-2-methyl-4-oxoquinazolin-6-ylmethyl)-
N-(prop-2-ynyl)amino]benzoyl-L-γ-4-methylglutamyl-
L-glutamic acid (1) α-tert-Butyl-γ-methyl-N-trityl-L-4-methylglutamate.

γ-Methyl-L-glutamate (12.88 g), tert-butyl acetate (500 ml) and 70% aqueous perchloric acid (12.6 g) were stirred at room temperature for 88 hours. The mixture was then cooled in an ice-water bath and extracted with cold 0.5N hydrochloric acid (3×130 ml). The combined aqueous extracts were immediately neutralised with solid sodium bicarbonate and then extracted with diethyl ether (3×200 ml). The ether extracts were combined, dried over anhydrous sodium sulphate, filtered and the solution concentrated in vacuo to give α-tert-butyl-γ-methyl-L-glutamate (14.5 g) as a colourless oil.

To a stirred solution of α-tert-butyl-γ-methyl-L-glutamate (13.71 g) in dry chloroform (50 ml), triethylamine (8.49 g) was added followed by lead nitrate (8.34 g) and then a solution of trityl chloride (11.67 g) in dry chloroform (20 ml). After stirring at room temperature for 18 hours a white solid had precipitated from the solution. This was removed by filtration, the filtrate concentrated in vacuo and the orange residue purified by chromatography on a silica gel column using a gradient of dichloromethane in hexane (10–100%) as eluant. There was thus obtained α-tert-butyl-γ-methyl-N-trityl-L-glutamate (9.46 g) as an oil, which solidified on standing at −20° C. for 4 weeks, m.p. 79°–80° C.

NMR Spectrum: (CD$_3$SOCD$_3$) 1.13 (s, 9H, C(CH$_3$)$_3$), 1.80, 1.92 (2×m, 2H, β-CH$_2$), 2.18, 2.44 (2×m, 2H, γ-CH$_2$), 2.79 (d, J=9.0 Hz, 1H, NH), 3.17 (m, 1H, α-CH), 3.60 (s, 3H, OCH$_3$), 7.16–7.41 (m, 15H, TrH).

Mass Spectrum: (CI) m/e 460 (M+H)$^+$.

Elemental Analysis: Found C, 76.13; H, 7.29;N, 2.89%. C$_{29}$H$_{33}$NO$_4$ requires C, 75.79; H, 7.24;N, 3.05%.

To a stirred solution of 0.6M potassium hexamethyldisilazide in tetrahydrofuran (13.75 ml) at −78° C. and under argon was added a solution of α-tert-butyl-γ-methyl-N-trityl-L-glutamate (2.52 g), in dry tetrahydrofuran (25 ml) over a 5 minute period. The resulting yellow solution was stirred at −78° C. for 50 minutes and then methyl iodide (1.56 g) was added. Stirring was continued at −78° C. for 1.25 hours and the white slurry was then poured into a saturated solution of ammonium chloride (200 ml). The mixture was extracted with diethyl ether (2×200 ml), the ether extracts were combined, dried over anhydrous sodium sulphate, filtered and the solution concentrated in vacuo. The residue was purified by chromatography on a silica gel column using a gradient of ethyl acetate in hexane (3–9%) as eluant. There was thus obtained α-tert-butyl-γ-methyl-N-trityl-L-4-methylglutamate (1.62 g) as a viscous oil, being a mixture of the two diastereoisomers (2S, 4S and 2S, 4R).

NMR Spectrum: (CD$_3$SOCD$_3$) 0.98, 1.04 (2×d, J=7.0 Hz, 3H, γ-CH$_3$), 1.12, 1.14 (2×s, 9H, C(CH$_3$)$_3$), 1.38, 1.54 (2×m, 1H, β-CH), 1.93, 2.10 (2×m, 1H, β-CH), 2.40 (m, 1H, γ-CH), 2.75, 2.80 (2×d, J$_1$=8.9 Hz, J$_2$=9.4 Hz, 1H, NH), 3.10 (m, 1H, α-CH), 3.50, 3.66 (2×s, 3H, CO$_2$CH$_3$), 7.16–7.39 (m, 15H, TrH).

Mass Spectrum: (CI) m/e 474 (M+H)$^+$.

Elemental Analysis: Found C, 76.12; H, 7.61; N, 2.89%. C$_{30}$H$_{35}$NO$_4$ requires C, 76.08; H, 7.45; N, 2.96%.

(2) Tri-tert-butyl-L-γ-4-methyl glutamyl-L-glutamate

To a mixture of lithium hydroxide monohydrate (0.117 g) in water (1.86 ml) was added a solution of α-tert-butyl-γ-methyl-N-trityl-L-4-methylglutamate (1.1 g) in tetrahydrofuran (27 ml). The resulting mixture was refluxed for 3 hours, then more water (0.6 ml) was added and refluxing continued for 5 hours. The organic solvent was then removed by evaporation, the residue was treated with a saturated sodium bicarbonate solution (100 ml) and the resulting mixture was acidified to pH 6 using dilute hydrochloric acid. The mixture was extracted with ethyl acetate (2×100 ml), the extracts combined, dried over anhydrous sodium sulphate, filtered and concentrated in vacuo. The residue was dried over phosphorus pentoxide in a vacuum dessicator overnight to give α-tert-butyl-N-trityl-L-4-methylglutamate (1.06 g) as a white foam.

To a stirred solution of α-tert-butyl-N-trityl-L-4-methylglutamate (0.76 g) and N-methylmorpholine (0.151 g) in dry tetrahydrofuran (3.5 ml) cooled to −20° C. was added isobutyl chloroformate (0.204 g). After 10 minutes a mixture of di-tert-butyl-L-glutamate hydrochloride (0.442 g) and N-methylmorpholine (0.151 g) in dry tetrahydrofuran (4.5 ml) was added. Stirring was continued at −20° C. for 10 minutes and then for 1.5 hours while the mixture was allowed to warm to room temperature. N-Methylmorpholine hydrochloride was filtered off and the filtrate concentrated in vacuo. The residue was purified by chromatography on a silica gel column using a gradient of ethyl acetate in distilled petrol (7–20%) as eluant. The product solidified on drying over phosphorus pentoxide in vacuo overnight. There was thus obtained tri-tert-butyl-N-[ N-(trityl)-L-γ-4-methylglutamyl]-L-glutamate (0.669 g), m.p. 58°–66° C.

NMR Spectrum: (CD$_3$SOCD$_3$) 0.94 (d, J=6.8 Hz, 3H, 4-Meglu γ-CH$_3$), 1.14 (s, 9H, 4-Meglu C(CH$_3$)$_3$), 1.39 (m, 19H, glu C(CH$_3$)$_3$ and 4-Meglu β-CH), 1.85, 2.11 (2×m, 3H, 4-Meglu β-CH and glu β-CH$_2$), 2.27 (t, J=7.6 Hz, 2H, glu γ-CH$_2$), 2.38 (m, 1H, 4-Meglu γ-CH), 2.68 (d, J=9.0 Hz, 1H, 4-Meglu NH), 3.04 (m, 1H, 4-Meglu α-CH), 4.13 (m, 1H, glu α-CH), 7.14–7.41 (m, 15H, TrH), 8.14 (d, J=7.4 Hz, 1H, glu NH).

Mass Spectrum: (CI) m/e 701 (M+H)$^+$.

Elemental Analysis: Found C, 72.02; H, 8.02, N, 3.87%. C$_{42}$H$_{56}$N$_2$O$_7$ requires C, 71.97; H, 8.05; N, 4.00%.

A solution of tri-tert-butyl-N-[ N-(trityl)-L-γ-4-methylglutamyl]-L-glutamate (0.608 g) in ethyl acetate (60 ml) containing 10% Pd/C (0.160 g) was stirred under hydrogen for 26 hours. Then more catalyst (0.035 g) was added and stirring continued under hydrogen for 20 hours. The catalyst was removed by filtration and the filtrate concentrated in vacuo to give a white semisolid, a mixture of triphenylmethane and tri-tert-butyl-L-γ-4-methylglutamyl-L-glutamate (0.450 g).

(3) N-p-[N-(3,4-Dihydro-2-methyl-4-oxoquinazolin-6-ylmethyl)-N-(prop- 2-ynyl)amino]benzoyl-L-γ-4-methylglutamyl-L-glutamic acid.

To a stirred solution of tri-tert-butyl-L-γ-4-methylglutamyl-L-glutamate (0.430 g) in dry dimethylformamide (6.5 ml) cooled to 0° C. was added p-[ N-(3,4-dihydro-2-methyl-4-oxoquinazolin-6-ylmethyl)-N-(prop-2-ynyl)amino]benzoic acid, trifluoroacetate salt (0.327 g), then diethyl cyanophosphonate (0.231 g) and triethylamine (0.143 g). The resulting solution was stirred in the dark at 0° C for 30 minutes and then for 1.5 hours at room temperature. Ethyl acetate (100 ml) and water (100 ml) were then added to the reaction mixture. The two layers were separated and the aqueous layer extracted with more ethyl acetate (2×100 ml). The combined ethyl acetate extracts were washed with 10% aqueous citric acid (2×100 ml), a saturated sodium bicarbonate solution (150 ml), a dilute aqueous sodium chloride solution (150 ml), water (100 ml) and then dried over anhydrous sodium sulphate, filtered and the ethyl acetate removed in vacuo. The residue was purified by chromatography on a silica gel column using a gradient of methanol in ethyl acetate (0–2%) as eluant. The product was precipitated from diethyl ether/petroleum ether at −20° C. and there was thus obtained tri-tert-butyl-N-p-[N-(3,4 -dihydro-2-methyl-4-oxoquinazolin-6-ylmethyl)-N-(prop-2-ynyl)amino]benzoyl-L-γ-4-methylglutamyl-L-glutamate (0.170 g), m.p. 102°–110° C.

NMR Spectrum: (CD$_3$SOCD$_3$) 1.03 (d, J=6.81 Hz, 3H, 4 -Meglu γ-CH$_3$), 1.33, 1.36, 1.38 (3×s, 27H, C(CH$_3$)$_3$), 1.65, 1.83, 2.05 (3×m, 4H, β-CH$_2$), 2.20 (t, J=7.7 Hz, 2H, glu γ-CH$_2$), 2.32 (s, 3H, quinazoline 2-CH$_3$), 2.50 (m, DMSO peak and 4-Meglu γ-CH), 3.22 (s, 1H, C≡CH), 4.07 (m, 1H, glu α-CH), 4.21 (m, 1H, 4-Meglu α-CH), 4.34 (s, 2H, CH$_2$C≡C), 4.78 (s, 2H, quinazoline 6-CH$_2$), 6.82 (d, J=8.7 Hz, 2H, 3',5'-ArH) 7.54 (d, J=8.4 Hz, 1H, quinazoline 8-H), 7.68 (m, 3H, quinazoline 7-H and 2',6'-ArH), 7.96 (s, 1H, quinazoline 5-H), 8.06 (d, J=7.6 Hz, 1H, glu NH), 8.20 (d, J=7.7 Hz, 1H, 4-Meglu$_L$ NH) 12.18 (s, 1H, lactam NH).

Mass Spectrum: (ESI) m/e 788 (M+H)$^+$.

Elemental Analysis: Found C, 64.91; H, 7.27; N, 8.79%. C$_{43}$H$_{57}$N$_5$O$_9$.0.5H$_2$O requires C, 64.81; H, 7.33; N, 8.79%.

Tri-tert-butyl-N-p-[N-(3,4-dihydro-2-methyl- 4-oxoquinazolin-6-ylmethyl)- N-(prop-2-ynyl)amino]benzoyl-L-γ- 4-methylglutamyl-L-glutamate (0.071 g) was treated with trifluoroacetic acid (6 ml) as described in Example 1(3) for the L-γ-glutamyl-N-methyl-L-glutamate analogue. There was thus obtained N-p-[N-(3,4 -dihydro-2-methyl-4-oxoquinazolin-6-ylmethyl)-N-(prop- 2-ynyl)amino]benzoyl-L-γ-4-methylglutamyl-L-glutamic acid (containing 0.95 equivalents of trifluoroacetic acid, 0.4 equivalents of diethyl ether and 1.2 equivalents of water; 0.053 g), m.p. 160°–165° C. (dec).

NMR Spectrum: 1.02 (d, J=6.8 Hz, 3H, 4-Meglu γ-CH$_3$), 1.65, 1.91, 2.09 (3×m, 4H, β-CH$_2$), 2.25 (t, J=7.6 Hz, 2H, glu γ-CH$_2$), 2.39 (s, 3H, quinazoline 2-CH$_3$), 2.50 (DMSO peak and 4-Meglu γ-CH), 3.23 (s, 1H, C≡CH), 4.19 (m, 2H, glu α-CH and 4-Meglu α-CH), 4.35 (s, 2H, CH$_2$C≡CH), 4.80 (s, 2H, quinazoline 6-CH$_2$), 6.82 (d, J=8.9 Hz, 2H, 3',5'-ArH), 7.58 (d, J=8.,4 Hz, 1H, quinazoline 8-H), 7.74 (d, J=8.7 Hz, 3H, quinazoline 7-H and 2',6'-ArH), 7.99 (s, 1H, quinazoline 5-H), 8.10 (d, J=7.7 Hz, 1H, glu NH), 8.26 (d, J=7.7 Hz, 1H, 4-Meglu NH).

Mass Spectrum: (ESI) m/e 620 (M+H)$^+$.

Elemental Analysis: Found C, 53.05; H, 5.46; N, 8.97; F, 6.89%. C$_{31}$H$_{33}$N$_5$O$_9$.0.95 CF$_3$COOH.0.4 Et$_2$O.1.2H$_2$O requires C, 53.18; H, 5.22; N, 8.99; F.6.95%.

Example 6

N-p-[N-(3,4-Dihydro-2-methyl- 4-oxoquinazolin-6-ylmethyl)- N-(prop-2-ynyl)amino]benzoyl-L-γ-4,4- dimethylglutamyl-L-glutamic acid (1) α-tert-Butyl-γ-allyl- N-trityl-L-4,4-dimethylglutamate.

To a stirred suspension of L-glutamic acid (8.82 g) in dry allyl alcohol (300 ml) chlorotrimethylsilane (19 ml) was added dropwise under an argon atmosphere. The mixture was stirred at room temperature for 18 hours and then diethyl ether (2 liters) was added to give a white precipitate. This was collected by filtration, washed with more diethyl ether and dried in vacuo over phosphorus pentoxide. There was thus obtained γ-allyl-L-glutamate hydrochloride (10.1 g) as as white solid, m.p. 132°–133° C. (decomp).

NMR Spectrum: (CD$_3$SOCD$_3$) 2.05 (m, 2H, β-CH$_2$), 2.54 (m, 2H, γ-CH$_2$), 3.90 (t, J=6.3 Hz, 1H, α-CH), 4.55 (dm, J=5.4 Hz, 2H, CH$_2$CH=CH$_2$), 5.20 (dm, J=9.3 Hz, 1H, CH=CH$_2$ cis), 5.30 (dm, J=16.3 Hz, 1H, CH=CH$_2$ trans), 5.93 (m, 1H, CH=CH$_2$), 8.52 (bd s, 3H, NH$_3$).

Mass Spectrum: (CI) m/e 188 (M—Cl).

γ-Allyl-L-glutamate hydrochloride (8.94 g), t-butyl acetate (250 ml) and 70% aqueous perchloric acid (6.3 g) were stirred at room temperature for 100 hours. The mixture was then cooled in an ice-water bath and extracted with cold 0.5N hydrochloric acid (3×80 ml). The combined aqueous extracts were immediately neutralised using solid sodium bicarbonate and then extracted with diethyl ether (3×120 ml). The extracts were combined, dried over anhydrous sodium sulphate, filtered and concentrated in vacuo to give α-tert-butyl-γ-allyl-L-glutamate (10.0 g) as a colourless oil.

To a stirred solution of α-tert-butyl-γ-allyl-L-glutamate (8.4 g) in dry chloroform (35 ml), triethylamine (5.25 g) was added followed by a solution of trityl chloride (7.23 g) in chloroform (15 ml) and then lead nitrate (4.3 g). After stirring at room temperature for 17 hours a white solid had formed. The solid was removed by filtration, the filtrate concentrated in vacuo and the residue was treated with hexane (40 ml) and left in a fridge overnight. The hexane solution was then filtered, the filtrate concentrated in vacuo and the residue purified by chromatography on a silica gel column using a gradient of ethyl acetate in distilled petroleum ether (4–6%) as eluant. There was thus obtained α-tert-butyl-γ-allyl-N-trityl-L-glutamate (8.10 g) as a yellow oil.

NMR Spectrum: (CD$_3$SOCD$_3$) 1.13 (s, 9H, C(CH$_3$)$_3$), 1.80, 1.90 (2×m, 2H, β-CH$_2$), 2.20, 2.46 (2×m, 2H, γ-CH$_2$), 2.80 (d, J=9.0 Hz, 1H, NH), 3.17 (m, 1H, α-CH), 4.54 (d, J=5.5 Hz, 2H, CO$_2$CH$_2$CH=CH$_2$), 5.20 (dm, J=10.4 Hz, 1H, CH=CH$_2$ cis), 5.29 (dm, J=15.8 Hz, 1H, CH=CH$_2$ trans), 6.88 (m, 1H, CH=CH$_2$), 7.15–7.40 (m, 15H, TrH).

Mass Spectrum: (CI) m/e 486 (M+H)$^+$.

Elemental Analysis: Found C, 76.46; H, 7.39; N, 2.82%. C$_{31}$H$_{35}$NO$_4$ requires C, 76.67; H, 7.26; N, 2.88%.

To a stirred solution of potassium hexamethyldisilazide (23.68 ml, 0.5M in toluene) in dry tetrahydrofuran (22 ml) at −78° C. and under argon was added a solution of α-tert-butyl-γ-allyl-N-trityl-L-glutamate (3.59 g) in dry tetrahydrofuran (26 ml) over a 5 minute period. The resulting yellow solution was stirred at −78° C. for 55 minutes and then methyl iodide (2.10 g) was added. Stirring was continued at −78° C. for 30 minutes and then the white slurry was poured into a saturated solution of ammonium chloride (200 ml). The resulting mixture was extracted with diethyl ether (3×150 ml), the ether extracts combined, dried over anhydrous sodium sulphate, filtered and concentrated in vacuo. The residue was purified by chromatography on a silica gel column using a gradient of ethyl acetate in petroleum ether (6–8%) as eluant. There was thus obtained α-tert-butyl-γ-allyl-N-trityl-L-4-methylglutamate (3.26 g) as an oil, being a mixture of the two diastereoisomers (2S, 4S) and (2S, 4R).

NMR Spectrum: (CD$_3$SOCD$_3$) 1.00, 1.07 (2×d, J=7.0 Hz, 3H, γ-CH$_3$), 1.12, 1.15 (2×s, 9H, C(CH$_3$)$_3$), 1.38, 1.57 (2×m, 1H, β-CH), 1.95, 2.15 (2×m, 1H, β-CH), 2.45 (m, 1H, γ-CH), 2.80 (t, J=9.4 Hz, 1H, NH), 3.12 (m, 1H, α-CH), 4.43 (ABdd, J$_1$=13.7 Hz, J$_2$=5.4 Hz, 1H, CH$_2$CH=CH$_2$), 4.60 (d, J=5.3 Hz, 1H, CH$_2$CH=CH$_2$), 5.10–5.35 (m, 2H, CH=CH$_2$), 5.70–6.00 (m, 1H, CH=CH$_2$), 7.16–7.40 (m, 15H, TrH).

Mass Spectrum: (CI) m/e 500 (M+H)$^+$.

Elemental Analysis: Found C, 75.74; H, 7.47; N, 2.73%. C$_{32}$H$_{37}$NO$_4$.0.4H$_2$O requires C, 75.83; H, 7.52; N, 2.76%.

To a stirred solution of potassium hexamethyldisilazide (16.2 ml, 0.5M in toluene) in dry tetrahydrofuran (16 ml) at −78° C. and under argon was added a solution of α-tert-γ-allyl-N-trityl-L-4-methylglutamate (2.24 g) in dry tetrahydrofuran (16 ml) over a 5 minute period. The resulting yellow solution was stirred at −78° C. for 55 minutes and then methyl iodide (1.12 ml) was added. Stirring was continued at −78° C. for 2 hours and then the yellow slurry was poured into a saturated solution of ammonium chloride (200 ml). The aqueous solution was extracted with diethyl ether (3×150 ml), the ether extracts combined, dried over anhydrous sodium sulphate, filtered and the solution concentrated in vacuo. The residue was purified by chromatography on a silica gel column using a gradient of ethyl acetate in distilled petroleum ether (3–6%). There was thus obtained α-tert-butyl-γ-allyl-N-trityl-L-4,4-dimethylglutamate (2.08 g) as a colourless oil.

NMR Spectrum: (CD$_3$SOCD$_3$) 0.94, 0.96 (2×s, 6H, γ-CH$_3$), 1.20 (s, 9H, C(CH$_3$)$_3$), 1.34 (dd, J$_1$=14.2 Hz, J$_2$=3.7 Hz, 1H, β-CH), 2.06 (dd, J$_1$=14.3 Hz, J$_2$=8.6 Hz, 1H, β-CH), 2.78 (d, J=8.9 Hz, 1H, NH), 3.09 (m, 1H, α-CH), 4.50 (ABddd, J$_1$=15.0 Hz, J$_2$=5.0 Hz, J$_3$=1.2 Hz, 2H, CH$_2$CH=CH$_2$), 5.16–5.30 (m, 2H, CH=CH$_2$), 5.87 (m, 1H, CH=CH$_2$), 7.16–7.40 (m, 15H, TrH).

Mass Spectrum: (CI) m/e 514 (M+H)$^+$.

Elemental Analysis: Found C, 75.96; H, 7.61; N, 2.66%. C$_{33}$H$_{39}$NO$_4$.0.5H$_2$O requires C, 75.83; H, 7.71; N, 2.68%.

(2) Tri-tert-butyl-L-γ-4-dimethylglutamyl-L-glutamate.

To a stirred solution of α-tert-butyl-γ-allyl-N-trityl-L-4,4-dimethylglutamate (1.4 g) in dry dichloromethane (11 ml) under argon was added tetrakis(triphenylphosphine)palladium(O) (0.091 g) and then pyrrolidine (0.35 ml). The resulting yellow solution was stirred at room temperature for 20 minutes and then diethyl ether (100 ml) and 1N hydrochloric acid (50 ml) were added. The two layers were separated and the aqueous layer washed with more diethyl ether (100 ml). The ether extracts were combined, dried over anhydrous sodium sulphate, filtered and concentrated in vacuo. The residue was treated with diethyl ether (30 ml), the yellow precipitate filtered off and the filtrate concentrated in vacuo to give α-tert-butyl-N-trityl-L-4,4-dimethylglutamate (1.25 g) as a white foam.

To a stirred solution of α-tert-butyl-N-trityl-L-4,4-dimethylglutamate (0.710 g) and (1H-1,2,3-benzotriazol-1-yloxy)tris(pyrrolidino)-phosphonium hexafluorophosphate (PyBOP) (0.935 g) in dry dichloromethane (1.9 ml) was added diisopropylethylamine (0.464 g) and then 4-dimethylaminopyridine (0.109 g) and di-tert-butyl-L-glutamate hydrochloride (0.531 g). After stirring at room temperature for 3 hours the solvent was removed by evaporation and the yellow residue purified by chromatography on a silica gel column using a gradient of ethyl acetate in hexane (5–20%) as eluant. There was thus obtained tri-tert-butyl-N-[N-(trityl-γ-4,4-dimethylglutamyl]-L-glutamate (0.445 g) as an oil.

NMR Spectrum: 0.80, 0.95 (2×s, 6H, 2×γ-CH$_3$), 1.19 (s, 9H, 4-diMeglu C(CH$_3$)$_3$), 1.34 (s, 9H, glu C(CH$_3$)$_3$), 1.39 (m, 10H, glu C(CH$_3$)$_3$ and 4-diMeglu β-CH), 1.78–1.98 (m, 3H, glu β-CH$_2$ and 4-diMeglu β-CH), 2.22 (t, J=7.2 Hz, 2H, glu γ-CH$_2$), 2.80 (d, J=8.2 Hz, 1H, 4-diMeglu NH), 2.98 (m, 1H, 4-diMeglu α-CH), 4.04 (m, 1H, glu α-CH), 7.14–7.40 (m, 15H, TrH).

Mass Spectrum: (CI) m/e 715 (M+H)$^+$.

Elemental Analysis: Found C, 71.65; H, 8.22; N, 3.84%. C$_{43}$H$_{58}$N$_2$O$_7$.0.3H$_2$O requires C, 71.70; H, 8.20; N, 3.89%.

A solution of tri-tert-butyl-N-[N-(trityl-L-γ-4,4-dimethylglutamyl]-L-glutamate (0.430 g) in ethyl acetate (50 ml) containing 10% Pd/C (0.065 g) was stirred under hydrogen for 26 hours. Then more catalyst (0.075 g) was added and stirring was continued under hydrogen for 16 hours. The catalyst was removed by filtration and the filtrate was concentrated in vacuo to give a white semisolid, a mixture of triphenylmethane and tri-tert-butyl-L-γ-4,4-dimethylglutamyl-L-glutamate (0.400 g).

(3) N-p-[N-(3,4-Dihydro-2-methyl-4-oxoquinazolin-6-ylmethyl)-N-(prop-2-ynyl)amino]benzoyl-L-γ-4,4-dimethylglutamyl-L-glutamic acid.

To a stirred solution of tri-tert-butyl-L-γ-4,4-dimethylglutamyl-L-glutamate (0.360 g) in dry dimethylformamide (7.0 ml) cooled to 0° C. under argon was added p-[

N-(3,4-dihydro-2-methyl- 4-oxoquinazolin-6-ylmethyl)-N-(prop-2-ynyl)amino]benzoic acid, trifluoroacetate salt (0.200 g) followed by diethyl cyanophosphonate (0.154 g) and triethylamine (0.095 g). The resulting solution was stirred in the dark at 0° C. for 10 minutes and then for 1.5 hours at room temperature. Ethyl acetate (70 ml) and water (70 ml) were then added to the reaction mixture. The two layers were separated and the aqueous layer was extracted with more ethyl acetate (2×50 ml). The combined ethyl acetate extracts were washed with a 10% aqueous citric acid solution (100 ml), saturated sodium bicarbonate solution (100 ml), dilute aqueous sodium chloride solution (100 ml) and water (100 ml), then dried over anhydrous sodium sulphate, filtered and concentrated in vacuo. The residue was purified by chromatography on a silica gel column using a gradient of methanol:ethyl acetate (0–2%) as eluant. The product was precipitated from diethyl ether/petroleum ether at −20° C. yielding tri-tert-butyl-N-p-[N-(3,4-dihydro-2-methyl-4-oxoquinazolin-6-ylmethyl)-N-(prop-2-ynyl)amino]benzoyl-L-γ-4,4-dimethylglutamyl-L-glutamate (0.200 g) as a white powder, m.p. 101°–104° C.

NMR Spectrum: (CD$_3$SOCD$_3$) 1.11, 1.16 (2×s, 6H, 4-diMeglu γ-CH$_3$), 1.30, 1.36 (2×s, 27H, C(CH$_3$)$_3$), 1.95 (m, 4H, β-CH$_2$), 2.21 (t, J=7.7 Hz, 2H, glu γ-CH$_2$), 2.32 (s, 3H, quinazoline 2-CH$_3$), 3.22 (s, 1H, C≡CH), 4.08 (m, 1H, glu α-CH), 4.23 (m, 1H, 4-diMeglu α-CH), 4.31 (s, 2H, CH$_2$C≡C), 4.76 (s, 2H, quinazoline 6-CH$_2$), 6.81 (d, J=8.7 Hz, 2H, 3',5'-ArH), 7.52 (d, J=8.4 Hz, 1H, quinazoline 8-H), 7.66 (m, 4H, quinazoline 7-H, 2',6'-ArH and 4-diMeglu NH), 7.95 (s, 1H, quinazoline 5-H), 8.19 (d, J=7.3 Hz, 1H, glu NH), 12.19 (s, 1H, lactam NH).

Mass Spectrum: (ESI) m/e 801 (M$^+$).

Elemental Analysis: Found C, 66.03; H, 7.68; N, 8.50%. C$_{44}$H$_{59}$N$_5$O$_9$ requires C, 65.90; H, 7.41; N, 8.73%.

Tri-tert-butyl-N-p-[N-(3,4-dihydro-2-methyl-4-oxoquinazolin- 6-ylmethyl)-N-(prop-2-ynyl)amino]benzoyl-L-γ-4,4-dimethylglutamyl-L-glutamate (0.068 g) was treated with trifluoroacetic acid (7 ml) as described in Example 1(3) for the L-γ-glutamyl-N-methyl-L-glutamate analogue. There was thus obtained N-p-[N-(3,4-dihydro-2-methyl- 4-oxoquinazolin-6-ylmethyl)-N-(prop-2-ynyl)amino]benzoyl-L-γ- 4,4-dimethyl-glutamyl-L-glutamic acid (containing 0.6 equivalents of trifluoroacetic acid and 0.8 equivalents of water; 0.050 g), m.p. >140° C. (dec).

NMR Spectrum (CD$_3$SOCD$_3$): 1.12, 1.17 (2×s, 6H, 4-diMeglu γ-CH$_3$), 1.84–2.13 (m, 4H, β-CH$_2$), 2.25 (t, J=7.4 Hz, 2H, glu γ-CH$_2$), 2.38 (s, 3H, quinazoline 2-CH$_3$), 3.23 (s, 1H, C≡CH), 4.20 (m, 1H, glu α-CH), 4.33 (m, 3H, CH$_2$C≡CH and 4-diMeglu α-CH), 4.79 (s, 2H, quinazoline 6-CH$_2$), 6.82 (d, J=8.6 Hz, 2H, 3',5'-ArH), 7.57 (d, J=8.4 Hz, 1H, quinazoline 8-H), 7.71 (m, 4H, quinazoline 7-H, 2',6'-ArH and 4-diMeglu NH), 7.99 (s, 1H, quinazoline 5-H), 8.22 (d, J=7.30 Hz, 1H, glu NH).

Mass Spectrum: (ESI) m/e 634 (M+H)$^+$.

Elemental Analysis: Found C, 55.71; H, 5.41; N, 9.60; F, 4.64%. C$_{32}$H$_{35}$N$_5$O$_9$.0.6TFA.0.8H$_2$O requires C, 55.66; H, 5.23; N, 9.77; F, 4.77%.

Example 7

N-p-[N-(3,4-Dihydro-2,7-dimethyl-4-oxoquinazolin-6-ylmethyl)-N-(prop-2-ynyl)amino]benzoyl-L-γ-glutamyl-N-methyl-L-glutamic acid The process described in Example 1(3) was repeated using N-p-[N-(3,4-dihydro-2,7-dimethyl-4-oxoquinazolin-6-ylmethyl)-N-(prop-2-ynyl)amino]benzoic acid, trifluoroacetic acid salt (0.475 g; prepared as described in Example 10 of UK Patent 2 202 847B) as starting material in place of N-p-[N-(3,4-dihydro-2-methyl- 4-oxoquinazolin-6-ylmethyl)-N-(prop-2-ynyl)amino]benzoic acid, trifluoroacetic acid salt. There was thus obtained tri-tert-butyl-N-p-[N-(3,4-dihydro-2,7-dimethyl-4-oxoquinazolin- 6-ylmethyl)-N-(prop-2-ynyl)amino]benzoyl-L-γ-glutamyl-N-methyl-L-glutamate (0.340 g), m.p. 114°–116° C.

NMR Spectrum: (CD$_3$SOCD$_3$) 1.36 (m, 27H, C(CH$_3$)$_3$), 1.74–2.20 (m) and 2.42 (m obscured) (8H, β-CH$_2$ and γ-CH$_2$), 2.31 (s, 3H, quinazoline 2-CH$_3$), 2.44 (s, 3H, quinazoline 7-CH$_3$), 2.62, 2.82 (2×s, 3H, N—CH$_3$), 3.15 (s, 1H, C≡CH), 4.26 (s, 2H, CH$_2$C≡C), 4.30 (m obscured, 1H, glu α-CH), 4.44, 4.79 (2×dd, J$_1$=10.58 Hz, J$_2$=4.86 Hz, 1H, N—Me glu α-CH), 4.66 (s, 2H, quinazoline 6-CH$_2$), 6.81 (d, J=8.95 Hz, 2H, 3',5'-ArH) 7.43 (s 1H quinazoline 8-H), 7.74 (d, J=7.74 Hz, 3H, quinazoline 5-H and 2',6'-ArH), 8.22 (t, J=7.44 Hz, 1H, glu NH), 12.00 (s, 1H, lactam NH).

Mass Spectrum: (ESI) m/e 802 (M+H)$^+$.

Elemental Analysis: Found C, 65.37; H, 7.35; N, 8.63%. C$_{44}$H$_{59}$N$_5$O$_9$.0.25H$_2$O requires: C, 65.53; H, 7.43; N, 8.68%.

A solution of tri-tert-butyl-N-p-[N-(3,4-dihydro-2,7-dimethyl-4-oxoquinazolin-6-ylmethyl)-N-(prop-2-ynyl)amino]benzoyl-L-γ-glutamyl-N-methyl-L-glutamate (0.200 g) in trifluoroacetic acid (15 ml) was stirred for 1.2 hours at room temperature in the dark. The solution was then concentrated in vacuo and the residue triturated with dry diethyl ether (20 ml). The white solid was isolated by filtration, washed with diethyl ether and dried in vacuo. There was thus obtained N-p-[N-(3,4-dihydro- 2,7-dimethyl-4-oxoquinazolin-6-ylmethyl)-N-(prop-2-ynyl)amino]benzoyl-L-γ-glutamyl-N-methyl-L-glutamic acid (0.180 g), m.p. 170° C. decomp.

NMR Spectrum: (CD$_3$SOCD$_3$) 1.82–2.23 (m) and 2.46 (m obscured) (8H, β-CH$_2$ and γ-CH$_2$), 2.23, 2.48 (2×s, 6H, quinazoline 2-CH$_3$ and quinazoline 7-CH$_3$), 2.65, 2.81 (2×s, 3H, N—CH$_3$), 3.23 (s, 1H, C≡CH), 4.31 (m, 3H, CH$_2$C≡C and glu α-CH), 4.56, 4.91 (2×dd, J$_1$=10.87 Hz, J$_2$=4.38 Hz, 1H, N—Me glu α-CH), 4.71 (s, 2H, quinazoline 6-CH$_2$), 6.79 (d, J=8.89 Hz, 2H, 3',5'-ArH), 7.48 (s, 1H, quinazoline 8-H), 7.76 (m, 3H, 2',6'-ArH and quinazoline 5-H), 8.33 (m, 1H, glu NH).

Mass Spectrum (ESI) m/e 634 (M+H)$^+$.

Elemental Analysis: Found C, 53.23; H, 5.00; N, 8.86; F, 7.33%. C$_{32}$H$_{35}$N$_5$O$_9$.1CF$_3$COOH.1H$_2$O requires: C, 53.33; H, 5.00; N, 9.15; F, 7.44%.

Example 8 n-p-[N-(3,4-Dihydro-2-methyl-4-oxoquinazolin-6-ylmethyl)-N-(prop-2-ynyl)amino]-o-fluorobenzoyl-L-γ-glutamyl-N-methyl-L-glutamic acid The process described in Example 1(3) was repeated using N-p-[N-(3,4-dihydro-2-methyl- 4-oxoquinazolin-6-ylmethyl)-N-(prop- 2-ynyl)amino]-o-fluorobenzoic acid, trifluoroacetic acid salt (0.479 g; prepared as described in Example 6 of UK Patent Application 2 253 849A) as starting material in place of N-p-[N-(3,4-dihydro-2-methyl-4-oxoquinazolin-6-ylmethyl)-N-(prop-2-ynyl)amino]benzoic acid, trifluoroacetic acid salt. There was thus obtained tri-tert-butyl-N-p-[N -(3,4- dihydro-2-methyl-4-oxoquinazolin-6-ylmethyl)-N-(prop-2-ynyl)amino]-o-fluorobenzoyl-L-γ-glutamyl-N-methyl-L-glutamate (0.430 g), m.p. 110°–112° C.

NMR Spectrum: (CD$_3$SOCD$_3$) 1.36 (m, 27H, C(CH$_3$)$_3$), 1.80–2.20, 2.42 (2×m, 8H, β-CH$_2$ and γ-CH$_2$), 2.33 (s, 3H, quinazoline 2-CH$_3$), 2.60, 2.80 (2×s, 3H, N—CH$_3$), 3.27 (s, 1H, C≡CH), 4.29 (m, 1H, glu α-CH), 4.37 (s, 2H, CH$_2$C≡C), 4.50 (dd) and 4.81 (dd obscured), (1H, J$_1$=10.15 Hz, J$_2$=4.78 Hz, N—Me glu α-CH), 4.79 (s, 2H, quinazoline 6-CH$_2$), 6.61 (d, J=14.56 Hz, 1H, 3'-ArH), 6.66 (d, J=8.63 Hz, 1H, 5'-ArH), 7.52 (m, 2H, 6'-ArH and quinazoline 8-H), 7.68 (dd, J$_1$=8.41 Hz, J$_2$=1.81 Hz, 1H, quinazoline 7-H), 7.95 (s, 1H, quinazoline 5-H), 8.02 (dd obscured) and 8.07 (dd) (1H, J$_1$=7.04 Hz, J$_2$=4.2 Hz, glu NH), 12.21 (s, 1H, lactam NH).

Mass Spectrum: (ESI) m/e 806 (M+H)$^+$.

Elemental Analysis: Found C, 63.68; H, 6.97; N, 8.62; F, 2.54%. C$_{43}$H$_{56}$FN$_5$O$_9$.0.25H$_2$O requires: C, 63.73; H, 7.03; N, 8.64; F, 2.34%.

A solution of tri-tert-butyl-N-p-[N-(3,4-dihydro-2-methyl-4-oxoquinazolin-6-ylmethyl)-N-(prop-2-ynyl)amino]-o-fluorobenzoyl-L-γ-glutamyl-N-methyl glutamate (0.220 g) in trifluoroacetic acid (15 ml) was stirred for 1.2 hours at room temperature in the dark. The solution was then concentrated in vacuo and the residue triturated with dry diethyl ether (20 ml). The white solid was isolated by filtration, washed with diethyl ether and dried in vacuo. There was thus obtained N-p-[N-( 3,4-dihydro-2-methyl-4-oxoquinazolin-6-ylmethyl)-N-(prop-2-ynyl)amino]-o-fluorobenzoyl-L-γ-glutamyl-N-methyl-L-glutamic acid (0.213 g), m.p. 120° C. decomp.

NMR Spectrum: (CD$_3$SOCD$_3$) 1.82–2.20 (m) and 2.41 (m obscured) (8H, β-CH$_2$ and γ-CH$_2$), 2.43 (s, 3H, quinazoline 2-CH$_3$), 2.63, 2.80 (2×s, 3H, N—CH$_3$), 3.27 (s, 1H, C≡CH), 4.37 (m, 3H, CH$_2$C≡C and glu α-CH), 4.54, 4.90 (2×dd, J$_1$=11.23 Hz, J$_2$=4.35 Hz, 1H, N—Me glu α-CH), 4.82 (s, 2H, quinazoline 6-CH$_2$), 6.61 (d, J=15.01 Hz, 1H, 3'-ArH), 6.66 (d, J=8.10 Hz, 1H, 5'-ArH), 7.52 (t, J=8.73 Hz, 1H, 6'-ArH), 7.61 (d, J=8.42 Hz, 1H, quinazoline 8-H), 7.77 (d, J=8.48 Hz, 1H, quinazoline 7-H), 8.00 (s, 1H, quinazoline 5-H), 8.05 (m, 1H, glu NH).

Mass Spectrum: (ESI) m/e 638 (M+H)$^+$.

Elemental Analysis: Found C, 50.45; H, 4.65; N, 8.22; F, 11.12%. C$_{31}$H$_{32}$FN$_5$O$_9$.1.3 CF$_3$COOH.1H$_2$O.1Et$_2$O requires: C, 50.47; H, 4.59; N, 8.55; F, 11.37%.

Example 9

N-p-[N-(3,4-Dihydro-2,7-dimethyl-4-oxoquinazolin-6-ylmethyl)-N-(prop-2-ynyl)amino]-o-fluorobenzoyl-L-γ-glutamyl-N-methyl-L-glutamic acid The process described in Example 1(3) was repeated using N-p-[N-(3,4-dihydro-2,7-dimethyl- 4-oxoquinazolin-6-ylmethyl)-N-(prop-2-ynyl)amino]-o-fluorobenzoic acid, trifluoroacetic acid salt (0.494 g; prepared as described in Example 7 of UK Patent Application 2 253 849A) as starting material in place of N-p-[N-(3,4-dihydro-2-methyl- 4-oxoquinazolin-6-ylmethyl)-N-(prop-2-ynyl)amino]benzoic acid, trifluoroacetic acid salt. There was thus obtained tri-tert-butyl-N-p-[N-(3,4-dihydro-2,7-dimethyl-4-oxoquinazolin-6-ylmethyl)-N-(prop-2-ynyl)amino]-o-fluorobenzoyl-L-γ-glutamyl-N-methyl-L-glutamate (0.400 g), m.p. 122°–124° C.

NMR Spectrum: (CD$_3$SOCD$_3$) 1.35 (m, 27H, C(CH$_3$)$_3$), 1.70–2.20 (m) and 2.40 (m obscured) (8H, β-CH$_2$ and γ-CH$_2$), 2.30 (s, 3H, quinazoline 2-CH$_3$), 2.43 (s, 3H, quinazoline 7-CH$_3$), 2.60, 2.80 (2×s, 3H, N—CH$_3$), 3.25 (s, 1H, C≡CH), 4.30 (m, 3H, CH$_2$C≡C and glu α-CH), 4.50, 4.79 (2×dd, J$_1$=10.68 Hz, J$_2$=4.61 Hz, 1H, N—Me glu α-CH), 4.68 (s, 2H, quinazoline 6-CH$_2$), 6.61 (m, 2H, 3',5'-ArH), 7.44 (s, 1H, quinazoline 8-H), 7.51 (t, J=8.67 Hz, 1H, 6'-ArH), 7.68 (s, 1H, quinazoline 5-H), 8.00, 8.08 (2×dd, J$_1$=6.98 Hz, J$_2$=4.30 Hz, 1H, glu NH), 12.10 (s, 1H, lactam NH).

Mass Spectrum: (ESI) m/e 820 (M+H)$^+$.

Elemental Analysis: Found C, 64.25; H, 7.10; N, 8.51; F, 2.36%. C$_{44}$H$_{58}$FN$_5$O$_9$ requires: C, 64.45; H, 7.13; N, 8.54; F, 2.32%.

A solution of tri-tert-butyl-N-p-[N-(3,4-dihydro-2,7-dimethyl-4-oxoquinazolin-6-ylmethyl)-N-(prop-2-ynyl)amino]-o-fluorobenzoyl-L-γ-glutamyl-N-methyl glutamate (0.215 g) in trifluoroacetic acid (16 ml) was stirred for 1.2 hours at room temperature in the dark. The solution was then concentrated in vacuo and the residue triturated with dry diethyl ether (20 ml). The white solid was isolated by filtration, washed with diethyl ether and dried in vacuo. There was thus obtained N-p-[N-(3,4-dihydro- 2,7-dimethyl-4-oxoquinazolin-6-ylmethyl)-N-(prop-2-ynyl)amino]-o-fluorobenzoyl-L-γ-glutamyl-N-methyl-L-glutamic acid (0.205 g), m.p. 150° C. decomp.

NMR Spectrum: (CD$_3$SOCD$_3$) 1.82–2.20 (m) and 2.46 (m obscured) (8H, β-CH$_2$ and γ-CH$_2$), 2.45, 2.48 (2×s, 6H, quinazoline 2-CH$_3$ and quinazoline 7-CH$_3$), 2.63, 2.81 (2×s, 3H, N—CH$_3$), 3.25 (s, 1H, C≡CH), 4.33 (m, 3H, CH$_2$C≡C and glu α-CH), 4.58, 4.90 (2×dd, J$_1$=10.94 Hz, J$_2$=4.43 Hz, 1H, N—Me glu α-CH), 4.74 (s, 2H, quinazoline 6-CH$_2$), 6.61 (m, 2H, 3',5'-ArH), 7.49 (s, 1H, quinazoline 8-H), 7.54 (t, J=8.73 Hz, 1H, 6'-ArH), 7.73 (s, 1H, quinazoline 5-H), 8.08 (m, 1H, glu NH).

Mass Spectrum: (ESI) m/e 652 (M+H)$^+$.

Elemental Analysis: Found C, 50.90; H, 4.52; N, 8.40; F, 11.58%. C$_{32}$H$_{34}$FN$_5$O$_9$.1.3 CF$_3$COOH. 1H$_2$O requires: C, 50.81; H, 4.60; N, 8.56; F, 11.38%.

Example 10

N-p-[N-(3,4-Dihydro-2,7-dimethyl-4-oxoquinazolin-6-ylmethyl)-N-methylamino]benzoyl-L-γ-glutamyl-N-methyl-L-glutamic acid The process described in Example 1(3) was repeated using N-p-[N-(3,4-dihydro-2,7-dimethyl-4-oxoquinazolin-6-ylmethyl)-N-methylamino]benzoic acid, trifluoroacetic acid salt (0.450 g; prepared as described in Example 11 of UK Patent Application 2 253 849A) as starting material in place of N-p-[N-(3,4-dihydro-2-methyl-4-oxoquinazolin-6-ylmethyl)-N-(prop-2-ynyl)amino]benzoic acid, trifluoroacetic acid salt. There was thus obtained tri-tert-butyl-N-p-[N-(3,4-dihydro- 2,7-dimethyl-4-oxoquinazolin-6-ylmethyl)-N-methylamino]benzoyl-L-γ-glutamyl-N-methyl-L-glutamate (0.260 g), m.p. 139°–140° C.

NMR Spectrum: (CD$_3$SOCD$_3$) 1.35 (m, 27H, C(CH$_3$)$_3$), 1.80–2.18 (m) and 2.40 (m obscured) (8H, β-CH$_2$ and γ-CH$_2$), 2.30 (s, 3H, quinazoline 2-CH$_3$), 2.43 (s, 3H, quinazoline 7-CH$_3$), 2.61, 2.81 (2×s, 3H, N—CH$_3$), 3.13 (s, 3H, 10-N-CH$_3$), 4.25 (m, 1H, glu α-CH), 4.69 (s, 2H, quinazoline 6-CH$_2$), 4.48, 4.80 (2×dd, J$_1$=10.72 Hz, J$_2$=4.66 Hz, 1H, N—Me glu α-CH), 6.70 (d, J=8.88 Hz, 2H, 3',5'-

ArH), 7.44, 7.53 (2×s, 2H, quinazoline 5-H and quinazoline 8-H), 7.71 (d, J=8.77 Hz, 2H, 2',6'-ArH), 8.24 (t, J=7.51 Hz, 1H, glu NH), 12.10 (s, 1H, lactam NH).

Mass Spectrum: (ESI) m/e 778 (M+H)⁺.

Elemental Analysis: Found C, 64.32; H, 7.58; N, 8.92%. $C_{42}H_{59}N_5O_9 \cdot 0.3H_2O$ requires: C, 64.40; H, 7.67; N, 8.94%.

Tri-tert-butyl-N-p-[N-(3,4-dihydro-2,7-dimethyl- 4-oxo-quinazolin-6-ylmethyl)-N-methylamino]benzoyl-L-γ-glutamyl-N-methyl-L-glutamate (0.135 g) in trifluoroacetic acid (12 ml) was stirred for 1.2 hours at room temperature in the dark. The solution was then concentrated in vacuo and the residue triturated with dry diethyl ether and dried in vacuo. There was thus obtained N-p-[N-(3,4-dihydro-2,7-dimethyl-4-oxoquinazolin- 6-ylmethyl)-N-methylamino]-benzoyl-L-γ-glutamyl-N-methyl-L-glutamic acid (0.120 g), m.p. 155° C. decomp.

NMR Spectrum: (CD₃SOCD₃) 1.80–2.16 (m) and 2.41 (m obscured) (8H, β-CH₂ and γ-CH₂), 2.40, 2.47 (2×s, 6H, quinazoline 2-CH₃ and quinazoline 7-CH₃), 2.64, 2.80 (2×s, 3H, N—CH₃), 3.13 (s, 3H, 10-N-CH₃), 4.31 (m, 1H, glu α-CH), 4.57, 4.91 (2×dd, J₁=11.0 Hz, J₂=4.31 Hz, 1H, N—Me glu α-CH), 4.72 (s, 2H, quinazoline 6-CH₂), 6.71 (d, J=8.71 Hz, 2H, 3',5'-ArH), 7.47, 7.53 (2×s, 2H, quinazoline 5H and quinazoline 8-H), 7.73 (d, J=8.53 Hz, 2H, 2',6'-ArH), 8.28 (d, J=7.18 Hz, H, glu NH).

Mass Spectrum: (ESI) m/e 610 (M+H)⁺.

Elemental Analysis: Found C, 51.29; H, 5.14; N, 9.00; F, 7.73%. $C_{30}H_{35}N_5O_9 \cdot 1CF_3COOH \cdot 1.5 H_2O$ requires: C, 51.20; H, 5.24; N, 9.33; F, 7.59%.

Example 11

N-p-[N-(3,4-Dihydro-2-methyl-4-oxoquinazolin-6-ylmethyl)-N-methylamino]-o-fluorobenzoyl-L-γ-glutamyl-N-methyl-L-glutamic acid The process described in Example 1(3) was repeated using N-p-[N-(3,4-dihydro-2-methyl- 4-oxoquinazolin-6-ylmethyl)-N-methylamino]-o-fluorobenzoic acid, trifluoroacetic acid salt (0.410 g; prepared as described in Example 12 of UK Patent Application 2 253 849A) in place of N-p-[N-( 3,4-dihydro-2-methyl-4-oxoquinazolin-6-ylmethyl)-N-(prop-2-ynyl)amino]benzoic acid, trifluoroacetic acid salt. There was thus obtained tri-tert-butyl-N-(3,4-dihydro-2-methyl-4-oxoquinazolin- 6-ylmethyl)-N-methylamino]-o-fluorobenzoyl-L-γ-glutamyl-N-methyl-L-glutamate (0.465 g), m.p. 107°–109° C.

NMR Spectrum: (CD₃SOCD₃) 1.35 (m, 27H, C(CH₃)₃), 1.80–2.18, 2.42 (2×m, 8H, β-CH₂ and γ-CH₂), 2.32 (s, 3H, quinazoline 2-CH₃), 2.60, 2.80 (2×s, 3H, N—CH₃), 3.13 (s, 3H, 10 -N—CH₃), 4.29 (m, 1H, glu α-CH), 4.49 (m) and 4.79 (m obscured) (1H, N—Me glu α-CH), 4.78 (s, 2H, quinazoline 6-CH₂), 6.54 (d, J=16.11 Hz, 1H, 3'-ArH), 6.61 (d, 9.33 Hz, 1H, 5'-ArH), 7.56 (m, 3H, 6'-ArH, quinazoline 7H and quinazoline 8-H), 7.84 (s, 1H, quinazoline 5-H), 7.87, 7.97 (2×t, J=6.20 Hz, 1H, glu NH), 12.22 (s, 1H, lactam NH).

Mass Spectrum: (ESI) m/e 782 (M+H)⁺.

Elemental Analysis: Found C, 62.70; H, 7.21; N, 9.02; F, 2.62%. $C_{41}H_{56}N_5O_9F$ requires: C, 62.98; H, 7.22; N, 8.96; F, 2.43%.

Tri-tert-butyl-N-p-[N-(3,4-dihydro-2-methyl- 4-oxo-quinazolin-6-ylmethyl)-N-methylamino]-o-fluorobenzoyl-L-γ-glutamyl-N-methyl-L-glutamate (0.295 g) in trifluoroacetic acid (23 ml) was stirred for 1.2 hours at room temperature in the dark. The solution was then concentrated in vacuo and the residue triturated with dry diethyl ether and dried in vacuo. There was thus obtained N-(3,4-dihydro-2-methyl-4-oxoquinazolin- 6-ylmethyl)-N-methylamino]-o-fluorobenzoyl-L-γ-glutamyl-N-methyl-L-glutamic acid (0.270 g), m.p. 110° C. decomp.

NMR Spectrum: (CD₃SOCD₃) 1.82–2.18 (m) and 2.40 (m obscured) (8H, β-CH₂ and γ-CH₂), 2.45 (s, 3H, quinazoline 2-CH₃), 2.63, 2.81 (2×s, 3H, N—CH₃), 3.13 (s, 3H, 10 -N—CH₃), 4.34 (m, 1H, glu α-CH), 4.53, 4.90 (2×dd, J₁=10.91 Hz, J₂=4.36 Hz, 1H, N—Me glu α-CH), 4.83 (s, 2H, quinazoline 6-CH₂), 6.56 (d, J=15.86 Hz, 1H, 3'-ArH), 6.62 (d, J=9.1 Hz, 1H, 5'-ArH), 7.53 (t, J=9.02 Hz, 1H, 6'-ArH), 7.62 (d, J=8.43 Hz, 1H, quinazoline 8-H), 7.70 (dd, J₁=8.43 Hz, J₂=1.82 Hz, 1H, quinazoline 7-H), 7.89 (d, J=1.52 Hz, 1H, quinazoline 5-H), 7.97 (t, J=5.50 Hz, glu NH).

Mass Spectrum: (ESI) m/e 614 (M+H)⁺.

Elemental Analysis: Found C, 48.32; H, 4.72; N, 8.12; F, 13.16%. $C_{29}H_{32}FN_5O_9 \cdot 1.6CF_3COOH \cdot 0.4Et_2O \; H_2O$ requires: C, 48.12; H, 4.73; N, 8.30; F, 13.05%.

Example 12

N-p-[N-(3,4-Dihydro-2,7-dimethyl-4-oxoquinazolin-6-ylmethyl)-N-methyl amino]-o-fluorobenzoyl-L-γ-glutamyl-N-methyl-L-glutamic acid The process described in Example 1(3) was repeated using N-p-[N-(3,4-dihydro-2,7-dimethyl-4-oxoquinazolin-6-ylmethyl)-N-methylamino]-o-fluorobenzoic acid, trifluoroacetic acid salt (0.478 g; prepared as described in Example 13 of UK Patent Application 2 253 849A) in place of N-p-[N-(3,4-dihydro- 2-methyl-4-oxoquinazolin-6-ylmethyl)-N-(prop-2-ynyl)amino]benzoic acid, trifluoroacetic acid salt. There was thus obtained tri-tert-butyl-N-p-[N-(3,4-dihydro-2,7-dimethyl-4-oxoquinazolin- 6-ylmethyl)-N-methylamino]-o-fluorobenzoyl-L-γ-glutamyl-N-methyl-L-glutamate (0.518 g), m.p. 162°–164° C.

NMR Spectrum: (CD₃SOCD₃) 1.36 (m, 27H, C(CH₃)₃), 1.73–2.18 (m) and 2.40 (m obscured) (8H, β-CH₂ and γ-CH₂), 2.30 (s, 3H, quinazoline 2-CH₃), 2.42 (s, 3H, quinazoline 7-CH₃), 2.60, 2.80 (2×s, 3H, N—CH₃), 3.11 (s, 3H, 10-N—CH₃), 4.29 (m, 1H, glu α-CH), 4.50, 4.79 (2×dd, J₁=10.72 Hz, J₂=4.53 Hz, 1H, N—Me glu α-CH), 4.69 (s, 2H, quinazoline 6-CH₂), 6.51 (d, J=14.38 Hz, 1H, 3'-ArH), 6.56 (d, J=8.10 Hz, 1H, 5'-ArH), 7.48 (m, 3H, 6'-ArH, quinazoline 5-H and quinazoline 8-H), 7.88, 7.98 (2×t, J=6.13 Hz, 1H, glu NH), 12.12 (s, 1H, lactam NH).

Mass Spectrum: (ESI) m/e 796 (M+H)⁺.

Elemental Analysis: Found C, 63.19; H, 7.31; N, 8.80; F, 2.44%. $C_{42}H_{58}N_5O_9F$ requires: C, 63.38; H, 7.34; N, 8.80; F, 2.39%.

Tri-tert-butyl-N-p-[ N-(3,4-dihydro-2,7-dimethyl-4-oxoquinazolin-6-ylmethyl)-N-methylamino]-o-fluorobenzoyl-L-γ-glutamyl-N-methylglutamate (0.296 g) was treated with trifluoroacetic acid (23 ml) and stirred for 1.2 hours at room temperature in the dark. The solution was then concentrated in vacuo and the residue triturated with dry diethyl ether and dried in vacuo. There was thus obtained N-p-[

N-(3,4-dihydro-2,7-dimethyl-4-oxoquinazolin-6-ylmethyl)-N-methylamino]-o-fluorobenzoyl-L-γ-glutamyl-N-methyl-L-glutamic acid (0.285 g), m.p. 155° C. decomp.

NMR Spectrum: (CD$_3$SOCD$_3$) 1.80–2.18 (m) and 2.40 (m obscured) (8H, β-CH$_2$ and γ-CH$_2$), 2.43, 2.47 (2×s, 6H, quinazoline 2-CH$_3$ and quinazoline 7-CH$_3$), 2.63, 2.81 (2×s, 3H, N—CH$_3$), 3.13 (s, 3H, 10-N—CH$_3$), 4.34 (m, 1H, glu$_L$ α-CH), 4.54, 4.90 (2×dd, J$_1$=10.98 Hz, J$_2$=4.43 Hz, 1H, N—Me glu α-CH), 4.73 (s, 2H, quinazoline 6-CH$_2$), 6.53 (d, J=13.10 Hz, 1H, 3'-ArH), 6.57 (d, J=6.90 Hz, 1H, 5'-ArH), 7.48, 7.50 (2×s, 2H, quinazoline 5-H and quinazoline 8-H), 7.54 (t obscured), J=9.30 Hz, 1H, 6'-ArH), 7.09 (m, 1H, glu NH).

Mass Spectrum: (ESI) m/e 628 (M+H)$^+$.

Elemental Analysis: Found C, 49.73; H, 5.01; N, 8.16; F, 11.50%. C$_{30}$H$_{34}$FN$_5$O$_9$.1.4CF$_3$COOH.0.5Et$_2$O.1H$_2$O requires: C, 49.62; H, 5.07; N, 8.31; F, 11.72%.

We claim:

1. A quinazoline of the formula (I):

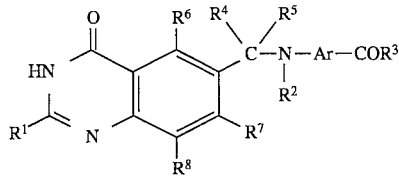

wherein R$^1$ is hydrogen or amino;
or R$^1$ is alkyl, alkoxy or alkylthio each of up to 6 carbon atoms;
or R$^1$ is aryl or aryloxy, each of up to 10 carbon atoms;
or R$^1$ is halogeno, hydroxy or mercapto;
or R$^1$ is alkyl of up to 3 carbon atoms which bears one or more substituents selected from halogeno, hydroxy and alkanoylamino each of up to 6 carbon atoms;
or R$^1$ is alkoxy of up to 3 carbon atoms which bears one or more substituents selected from hydroxy and alkoxy of up to 6 carbon atoms;
wherein R$^2$ is hydrogen or alkyl, alkenyl, alkynyl, hydroxyalkyl, alkoxyalkyl, mercaptoalkyl, alkylthioalkyl, halogenoalkyl, cyanoalkyl, aminoalkyl, alkylaminoalkyl, dialkylaminoalkyl, alkanoylalkyl, carboxyalkyl, carbamoylalkyl or alkanoyl each of up to 6 carbon atoms;
wherein Ar is phenylene or heterocyclene which is unsubstituted or which bears one or more substituents selected from halogeno, cyano, nitro, hydroxy, amino and carbamoyl and alkyl, alkoxy, halogenoalkyl, alkanoylamino and alkoxycarbonyl each of up to 6 carbon atoms;
wherein R$^3$ is a group of formula

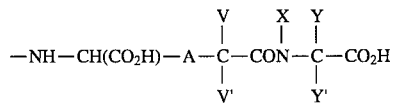

in which A is a carbon-carbon single bond or an alkylene group of up to 5 carbon atoms and V and V' are each separately hydrogen, or alkyl, alkenyl or alkynyl each of up to 6 carbon atoms;
X is hydrogen or alkyl, alkenyl or alkynyl each of up to 4 carbon atoms;
Y is hydrogen or alkyl, alkenyl or alkynyl each of up to 6 carbon atoms;

or X and Y together are a group (CH$_2$)$_n$ where n is 2, 3 or 4;
and Y' is hydrogen or alkyl, alkenyl or alkynyl each of up to 6 carbon atoms;
or Y' is alkyl of up to 6 carbon atoms which bears one or more substituents selected from amino, carboxy, hydroxy and mercapto;
or Y' is phenyl or benzyl; but with one or more of the following provisos:
(a) at least one of V and V' is other than hydrogen,
(b) X is other than hydrogen, and
(c) Y and Y' are each other than hydrogen;
wherein R$^4$ is hydrogen or alkyl of up to 4 carbon atoms;
wherein R$^5$ is hydrogen or alkyl of up to 4 carbon atoms; and
wherein each of R$^6$, R$^7$ and R$^8$ is hydrogen or alkyl or alkoxy each of up to 4 carbon atoms; or is halogeno; the quinazoline optionally being in the form of a pharmaceutically acceptable salt, ester or amide thereof.

2. A quinazoline according to claim 1, wherein R$^3$ is the residue of a dipeptide in which the first, N-terminal amino acid residue thereof attached to the carbonyl group of COR$^3$ is an amino acid residue

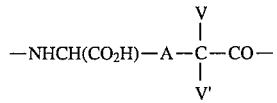

in which A is a carbon-carbon single bond or an alkylene group of up to 5 carbon atoms and, V and V' are each separately hydrogen, or alkyl, alkenyl or alkynyl each of up to 6 carbon atoms; and the second amino acid residue is of an α-amino acid substituted on the nitrogen atom by an alkyl, alkenyl or alkynyl group of up to 4 carbon atoms, by an alkyl group of up to 3 carbon atoms which bears one or more halogeno group substituents or a hydroxy group substituent, or by an ethylene, trimethylene or tetramethylene group linked to the α-carbon atom thereof.

3. A compound being:
N-p-[N-(3,4-dihydro-2-amino-4-oxoquinazolin-6-ylmethyl)-N-methylamino]-o-fluorobenzoyl-L-γ-glutamyl-N-methyl-L-glutamic acid,
N-p-[N-(3,4-dihydro-2-amino-4-oxoquinazolin-6-ylmethyl)-N-ethylamino]-o-fluorobenzoyl-L-γ-glutamyl-N-methyl-L-glutamic acid,
N-p-[N-(3,4-dihydro-2-amino-4-oxoquinazolin-6-ylmethyl)-N-(prop-2-ynyl)amino]-o-fluorobenzoyl-L-γ-glutamyl-N-methyl-L-glutamic acid,
N-p-[N-(3,4-dihydro-2-methyl-4-oxoquinazolin-6-ylmethyl)-N-methylamino]-o-fluorobenzoyl-L-γ-glutamyl-N-methyl-L-glutamic acid,
N-p-[N-(3,4-dihydro-2-methyl-4-oxoquinazolin-6-ylmethyl)-N-ethylamino]-o-fluorobenzoyl-L-γ-glutamyl-N-methyl-L-glutamic acid,
N-p-[N-(3,4-dihydro-2-methyl-4-oxoquinazolin-6-ylmethyl)-N-(prop-2-ynyl)amino]-o-fluorobenzoyl-L-γ-glutamyl-N-methyl-L-glutamic acid,
N-p-[N-(3,4-dihydro-2,7-dimethyl-4-oxoquinazolin-6-ylmethyl)-N-methylamino]-o-fluorobenzoyl-L-γ-glutamyl-N-methyl-L-glutamic acid,
N-p-[N-(3,4-dihydro-2,7-dimethyl-4-oxoquinazolin-6-ylmethyl)-N-ethylamino]-o-fluorobenzoyl-L-γ-glutamyl-N-methyl-L-glutamic acid, N-p-[
N-(3,4-dihydro-2,7-dimethyl-4-oxoquinazolin-6-ylmethyl)-
N -(prop-2-ynyl)amino]-o-fluorobenzoyl-L-γ-glutamyl-
N-methyl-L-glutamic acid,
N-p-[N-(3,4-dihydro-2-methoxy-4-oxoquinazolin-6 -ylm-
ethyl)-N-methylamino]-o-fluorobenzoyl-L-γ-glutamyl-
N-methyl-L-glutamic acid,
N-p-[N-(3,4-dihydro-2-methoxy-4-oxoquinazolin-6 -ylm-
ethyl)-N-ethylamino]-o-fluorobenzoyl-L-γ-glutamyl-
N-methyl-L-glutamic acid, or
N-p-[N-(3,4-dihydro-2-methoxy-4-oxoquinazolin-6 -ylm-
ethyl)-N-(prop-2-ynyl)amino]-
o-fluorobenzoyl-L-γ-glutamyl-N-methyl-L-glutamic
acid;
or a pharmaceutically acceptable salt, ester or amide thereof.

4. A quinazoline according to claim 1, wherein A-CV(V') is a group A' in which A' is an alkylene group of up to 6 carbon atoms.

5. A quinazoline according to claim 4, wherein A' is $CH_2$, $CH_2CH_2$, $CH_2CH_2CH_2$, $CH(CH_3)CH_2$, $CH_2CH(CH_3)$ or $CH_2C(CH_3)_2$.

6. A quinazoline according to claim 1, wherein X is methyl or ethyl, or X and Y together form a group $(CH_2)_3$.

7. A quinazoline according to claim 1, wherein Y is hydrogen, methyl or ethyl, or X and Y together form a group $(CH_2)_3$.

8. A quinazoline according to claim 1, wherein A-CV(V') is $CH_2CH_2$, X is methyl and Y is hydrogen.

9. A quinazoline according to claim 1, wherein $R^3$ is a group of the formula

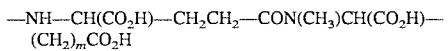

in which m is 1, 2 or 3.

10. A quinazoline according to claim 1, wherein $R^1$ is hydrogen, amino, methyl, ethyl, isopropyl, methoxy, ethoxy, methylthio, phenyl, tolyl, phenoxy, chloro, bromo, hydroxy, mercapto, fluoromethyl, difluoromethyl, trifluoromethyl, chloromethyl, hydroxymethyl, acetamidomethyl, 2-hydroxyethoxy, 2-methoxyethoxy or 2-ethoxyethoxy;
wherein $R^2$ is hydrogen, methyl, ethyl, propyl, prop-2-enyl, but-2-enyl, prop-2-ynyl, but-2-ynyl, 2-hydroxyethyl, 3-hydroxypropyl, 2-methoxyethyl, 3-methoxypropyl, 2-mercaptoethyl, 2-methylthioethyl, 2-fluoroethyl, 2-chloroethyl, 2-bromoethyl, 3-fluoropropyl, cyanomethyl, 2-cyanoethyl, 2-aminoethyl, 2-methylaminoethyl, 2-dimethylaminoethyl, acetonyl, carboxymethyl, carbamoylmethyl or acetyl;
wherein Ar is 1,4-phenylene, thienylene, pyridylene, pyrimidinylene, thiazolylene or oxazolylene which is unsubstituted or which bears one or two substituents selected from fluoro, chloro, bromo, phenyl, cyano, nitro, hydroxy, amino, carbamoyl, methyl, ethyl, methoxy, ethoxy, fluoromethyl, difluoromethyl, trifluoromethyl or acetamido;
wherein $R^4$ is hydrogen, methyl or ethyl;
wherein $R^5$ is hydrogen, methyl or ethyl; and
wherein each of $R^6$, $R^7$ and $R^8$ is hydrogen, methyl, ethyl, methoxy, ethoxy, fluoro, chloro or bromo.

11. A quinazoline according to claim 1, wherein $R^1$ is hydrogen, amino, methyl, ethyl or methoxy;
wherein $R^2$ is methyl, ethyl, prop-2-enyl, prop-2-ynyl, 2-hydroxyethyl, 3-hydroxypropyl, 2-fluoroethyl or acetonyl;
wherein Ar is 1,4-phenylene, 2-fluoro-1,4-phenylene or 2,6-difluoro-1,4-phenylene;

wherein $R^3$ is a group of formula

in which m is 1, 2 or 3;
wherein $R^4$ is hydrogen or methyl;
wherein $R^5$ is hydrogen;
wherein $R^6$ is hydrogen or chloro;
wherein $R^7$ is hydrogen, methyl, fluoro or chloro; and
wherein $R^8$ is hydrogen, methoxy or chloro.

12. A quinazoline according to claim 1, wherein $R^1$ is amino, methyl or methoxy;
wherein $R^2$ is methyl, ethyl, prop-2-enyl, prop-2-ynyl, 2-hydroxyethyl, 3-hydroxypropyl, 2-fluoroethyl or acetonyl;
wherein Ar is 1,4-phenylene, 2-fluoro-1,4-phenylene or 2,6-difluoro-1,4-phenylene;
wherein $R^3$ is the residue of the dipeptide γ-glutamyl-N-methyl-2-aminoadipic acid or γ-glutamyl-N-methylglutamic acid;
wherein $R^4$ is hydrogen or methyl;
wherein $R^5$ is hydrogen;
wherein $R^6$ is hydrogen or chloro;
wherein $R^7$ is hydrogen, methyl, fluoro or chloro; and
wherein $R^8$ is hydrogen, methoxy or chloro.

13. A quinazoline according to claim 1, wherein the first amino acid residue of the group R is of the L configuration about the α-carbon atom thereof and the second amino acid residue is also of the L configuration about the α-carbon atom thereof when that atom is asymmetric.

14. A quinazoline according to claim 1 wherein $R^1$ is methyl;
wherein $R^2$ is methyl or prop-2-ynyl;
wherein Ar is 1,4-phenylene or 2-fluoro-1,4-phenylene;
wherein $R^3$ is the residue of L-γ-glutamyl-N-methyl-L-glutamic acid;
wherein $R^4$ is hydrogen or methyl;
wherein $R^5$ is hydrogen;
wherein $R^6$ is hydrogen or chloro;
wherein $R^7$ is hydrogen, methyl, methoxy, fluoro or chloro; and
wherein $R^8$ is hydrogen, methyl, methoxy or chloro.

15. A compound being:
N-p-[N-(3,4-dihydro-2-methyl-4-oxoquinazolin-6 -ylmethyl)-N-methylamino]benzoyl-L-γ-glutamyl-
N-methyl-L-glutamic acid,
N-p-[
N-(3,4-dihydro-2-methyl-4-oxoquinazolin-6-ylmethyl)-
N-ethylamino]benzoyl-L-γ-glutamyl-
N-methyl-L-glutamic acid,
N-p-[
N-(3,4-dihydro-2-methyl-4-oxoquinazolin-6-ylmethyl)-
N -(prop-2-ynyl)amino]benzoyl-L-γ-glutamyl-
N-methyl-L-glutamic acid,
N-p-[
N-(3,4-dihydro-2-amino-4-oxoquinazolin-6-ylmethyl)-N
-methylamino]benzoyl-L-γ-glutamyl-
N-methyl-L-glutamic acid,
N-p-[
N-(3,4-dihydro-2-amino-4-oxoquinazolin-6-ylmethyl)-
N-ethylamino]benzoyl-L-γ-glutamyl-
N-methyl-L-glutamic acid,
N-p-[
N-(3,4-dihydro-2-amino-4-oxoquinazolin-6-ylmethyl)-N
-(prop-2-ynyl)amino]benzoyl-L-γ-glutamyl-
N-methyl-L-glutamic acid, N-p-[
N-(3,4-dihydro-2,7-dimethyl-4-oxoquinazolin-6-ylmethyl)-
N-methylamino]benzoyl-L-γ-glutamyl-
N-methyl-L-glutamic acid, N-p-[N-(3,4-dihydro-2,7-dimethyl-4-oxoquinazolin-6-ylm-
ethyl)-N-ethylamino]benzoyl-L-γ-glutamyl-
N-methyl-L-glutamic acid, N-p-[
N-(3,4-dihydro-2,7-dimethyl-4-oxoquinazolin-6-ylmethyl)-
N-(prop-2-ynyl)amino]benzoyl-L-γ-glutamyl-
N-methyl-L-glutamic acid, N-p-[N-(3,4-dihydro-2-methoxy-4-oxoquinazolin-6-ylm-
ethyl)-N-methylamino]benzoyl-L-γ-glutamyl-
N-methyl-L-glutamic acid, N-p-[N-(3,4-dihydro-2-methoxy-4-oxoquinazolin-6-ylm-
ethyl)-N-ethylamino]benzoyl-L-γ-glutamyl-
N-methyl-L-glutamic acid, or N-p[N-(3,4-dihydro-2-methoxy-4-oxoquinazolin-6-ylm-
ethyl)-N-(prop-2-ynyl)amino]benzoyl-L-γ-glutamyl-
N-methyl-L-glutamic acid;

or a pharmaceutically acceptable salt, ester or amide thereof.

16. A pharmaceutical composition comprising a quinazoline according to any of claims 1, 3 and 15 together with a pharmaceutically acceptable diluent or carrier.

17. A method for aiding regression and palliation of cancer in a patient in need of such treatment which comprises administering to said patient an effective amount of a quinazoline according to any of claims 1, 3 and 15.

* * * * *